(12) United States Patent
Kirkland et al.

(10) Patent No.: US 9,676,997 B2
(45) Date of Patent: Jun. 13, 2017

(54) COMPOSITIONS AND METHODS FOR STABILIZING LUMINOGENIC SUBSTRATES

(71) Applicant: Promega Corporation, Madison, WI (US)

(72) Inventors: Thomas Kirkland, Atascadero, CA (US); Keith V. Wood, Mount Horeb, WI (US); Mary Hall, Waunakee, WI (US); Marie Schwinn, Madison, WI (US)

(73) Assignee: PROMEGA CORPORATION, Madison, WI (US)

(*) Notice: Subject to any disclaimer, the term of this patent is extended or adjusted under 35 U.S.C. 154(b) by 0 days.

(21) Appl. No.: 14/721,727

(22) Filed: May 26, 2015

(65) Prior Publication Data

US 2015/0337198 A1    Nov. 26, 2015

Related U.S. Application Data

(60) Provisional application No. 62/002,363, filed on May 23, 2014.

(51) Int. Cl.
| | |
|---|---|
| *C07D 253/075* | (2006.01) |
| *C07D 487/04* | (2006.01) |
| *A61K 31/53* | (2006.01) |
| *A61K 31/4985* | (2006.01) |
| *C09K 11/06* | (2006.01) |
| *C12Q 1/66* | (2006.01) |

(52) U.S. Cl.
CPC .......... *C09K 11/06* (2013.01); *A61K 31/4985* (2013.01); *A61K 31/53* (2013.01); *C07D 253/075* (2013.01); *C07D 487/04* (2013.01); *C12Q 1/66* (2013.01); *C09K 2211/1007* (2013.01); *C09K 2211/1044* (2013.01)

(58) Field of Classification Search
CPC .............. C07D 253/075; C07D 487/04; A61K 31/4985; A61K 31/53
USPC .......................... 544/182, 350; 514/243, 249
See application file for complete search history.

(56) References Cited

U.S. PATENT DOCUMENTS

| | | | |
|---|---|---|---|
| 7,718,389 B2 * | 5/2010 | Ohmiya | ............... C12Q 1/66 435/8 |
| 8,809,529 B2 | 8/2014 | Klaubert et al. | |
| 2008/0020384 A1 | 1/2008 | Ohmiya et al. | |
| 2015/0064731 A1 | 3/2015 | Klaubert et al. | |

FOREIGN PATENT DOCUMENTS

DE    2000622    7/1971

OTHER PUBLICATIONS

International Search Report and Written Opinion for Application No. PCT/US2015/032439 dated Sep. 4, 2015 (9 pages).
Davydov et al., "Stabilisation of polyisoprene rubber with 3-mercapto-1,2,4-triazin-5-one derivatives", International Polymer Science and Technology, vol. 23, No. 11, 1996, pp. T63/T64.
Karimov et al., "Stabilization of poly (vinyl chloride) by 3-mercapto-1,2,4-triazin-5-one derivatives", Polymer Degradation and Stability, vol. 52, No. 2, 1996, pp. 197-199.
Liu et al., "Design, synthesis, and biological evaluation of 7H-thiazolo[3,2-b]-1,2,4-triazin-7-one derivatives as novel acetylcholinesterase inhibitors", ARKIVOC (2009) pp. 333-348.
Liu et al., "Design, synthesis, and biological evaluation of 7H-thiazolo[3,2-b]-1,2,4-triazin-7-onederivatives as acetylcholinesterase inhibitors", Letters in Drug Design and Discovery, (2010) 7, pp. 5-8.
Pustoshnaya et al., "Antioxidant 1-54 effect of triazinone derivatives in thermal oxidation of polyisoprene", Polymer Degradation and Stability, vol. 70, No. 1, 2000, pp. 39-41.
CAS RN 615-76-9, Sigma-Aldrich, catalog No. 275514 available online at:<http://www.sigmaaldrich.com/catalog/product/aldrich/275514?>.
CAS RN 7338-75-2, Sigma Aldrich, catalog No. S784028 available online at:<http://www.sigmaaldrich.com/catalog/product/aldrich/s784028?>.
CAS RN 84424-74-8, Sigma-Aldrich, catalog No. OTV000379 available online at:<http://www.sigmaaldrich.com/catalog/product/aldrich/otv000379?>.
CAS RN 58909-39-0, Sigma Aldrich, catalog No. 549746 available online at:<http://www.sigmaaldrich.com/catalog/product/aldrich/549746?>.
CAS RN 43076-59-1, Sigma Aldrich, catalog No. L125016 available online at:<http://www.sigmaaldrich.com/catalog/product/aldrich/l125016?>.
CAS RN 586-95-8, Sigma-Aldrich, catalog No. L151629 available online at:<http://www.sigmaaldrich.com/catalog/product/aldrich/l151629?>.
MDL MFCD01847282, Sigma Aldrich, catalog No. L150819 available online at:<http://www.sigmaaldrich.com/catalog/product/aldrich/l150819?>.
MDL MFCD01463040, Sigma Aldrich, catalog No. L151211 available online at:<http://www.sigmaaldrich.com/catalog/product/aldrich/l151211?>.

(Continued)

*Primary Examiner* — Venkataraman Balasubramanian
(74) *Attorney, Agent, or Firm* — Michael Best & Friedrich LLP

(57) ABSTRACT

Disclosed herein are compositions and methods for stabilizing a luminogenic substrate such as coelenterazine or a functional analog thereof. The functional analog may be furimazine. The composition may include the luminogenic substrate, a thionucleoside, and an organic solvent, in which the thionucleoside is present in an amount effective to stabilize the luminogenic composition against decomposition. The method provided herein stabilizes the luminogenic substrate against decomposition by contacting the luminogenic substrate with an effective amount of the thionucleoside in the presence of the organic solvent. Also provided herein is a kit containing the composition.

17 Claims, 22 Drawing Sheets

(56) References Cited

OTHER PUBLICATIONS

MDL MFCD01567017, Sigma Aldrich, catalog No. PH008592 available online at:<http://www.sigmaaldrich.com/catalog/product/aldrich/ph008592?>.
CAS RN 22278-81-5, Otava Chemicals, catalog No. 0107170001 available online at:<www.otavachemicals.com>.
CAS RN 1002103-80-1, Aurora Fine Chemicals, catalog No. A00.548.768 available online at<http://online.aurorafinechemicals.com/>.

* cited by examiner

COMPOSITIONS AND METHODS FOR STABILIZING LUMINOGENIC SUBSTRATES

CROSS-REFERENCE TO RELATED APPLICATIONS

This application claims priority to U.S. Provisional Patent Application No. 62/002,363, filed May 23, 2014, the entire contents of which are hereby incorporated by reference.

TECHNICAL FIELD

The present invention relates to compositions and methods for stabilizing luminogenic substrates.

BACKGROUND

Luminescence is often used in biological assays as a measure of the activity of a reporter molecule. The reporter molecule, in turn, links the luminescent measurement to a biological process of interest such as transcription (gene expression), translation (protein expression), protein-protein interactions, and so forth, thereby allowing for quantitative measurements of changes occurring in the biological process.

The reporter molecule is typically a luminogenic enzyme (e.g., firefly luciferase, *Renilla* luciferase, *Oplophorus* luciferase, etc.) that, when provided with its luminogenic substrate, results in the production of light, i.e., luminescence. The luminogenic substrate, however, can decompose during storage thereby resulting in loss of the substrate before addition to or use in the biological assay. Such decomposition can be the result of instability of the luminogenic substrate in solution over time in a temperature-dependent manner. This decomposition results in waste of the luminogenic substrate and reduced sensitivity and reproducibility of luminescent measurements derived from biological assays that employed the decomposed luminogenic substrate. Additionally, the products from this decomposition often inhibit the luminescent reaction.

Accordingly, the need exists for the identification and development of new compositions and/or methods for stabilizing a luminogenic substrate prior to its use in a luminescent reaction.

SUMMARY

The present disclosure provides a composition comprising: (a) a luminogenic substrate; (b) an effective amount of a compound of formula (I) or a tautomer thereof,

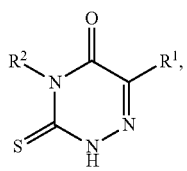

(I)

wherein
R$^1$ is hydrogen, alkyl, substituted alkyl, alkyl-aryl, alkyl-heteroaryl, cycloalkyl, aryl, heteroaryl, carboxylic acid, ester, NR$^a$R$^b$, imine, hydroxyl, or oxo;
R$^2$ is hydrogen, NR$^a$R$^b$, imine, alkyl, or aryl;
R$^a$ and R$^b$ are each independently hydrogen, alkyl, or aryl; and
(c) an organic solvent.

The present disclosure also provides a kit comprising the above composition in a single container, wherein the compound of formula (I) or tautomer thereof stabilizes the luminogenic substrate.

The present disclosure further provides a method for stabilizing a luminogenic substrate, the method comprising contacting the luminogenic substrate with an effective amount of a compound of formula (I) or a tautomer thereof in the presence of an organic solvent, whereby the luminogenic substrate is stabilized against decomposition, wherein the compound of formula (I) is

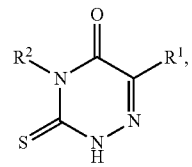

(I)

wherein
R$^1$ is hydrogen, alkyl, substituted alkyl, alkyl-aryl, alkyl-heteroaryl, cycloalkyl, aryl, heteroaryl, carboxylic acid, ester, NR$^a$R$^b$, imine, hydroxyl, or oxo;
R$^2$ is hydrogen, NR$^a$R$^b$, imine, alkyl, or aryl; and
R$^a$ and R$^b$ are each independently hydrogen, alkyl, or aryl.

BRIEF DESCRIPTION OF THE DRAWINGS

In FIG. 16, furimazine was at 37° C. in the presence and absence of ATT, and in the presence of different organic solvents (i.e., 50% polyethylene glycol (PG):50% ethanol; 60% polyethylene glycol (PG):40% ethanol; and 15% glycerol:85% ethanol).

DETAILED DESCRIPTION

Figure 1A:
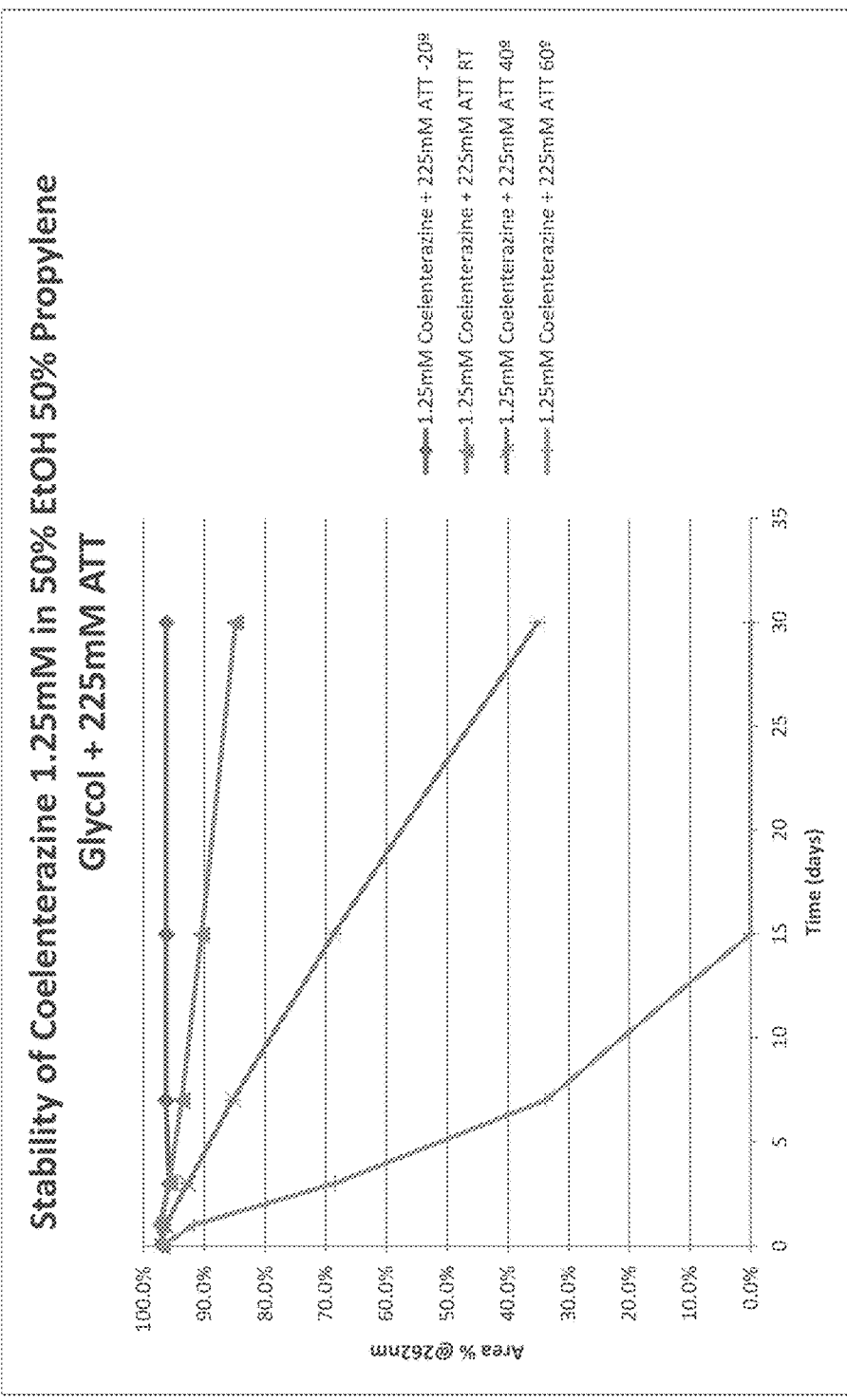
FIG. 1A shows the stability of coelenterazine in the presence of ATT.

The present invention relates to a composition for stabilizing a luminogenic substrate. The luminogenic substrate may be, but is not limited to, coelenterazine, coelenterazine-h, coelenterazine-h-h, furimazine, a derivative thereof, an analog thereof, or any combination thereof. The composition may include the luminogenic substrate, a thionucleoside, and an organic solvent. The composition may not include or contain a luminogenic enzyme.

The thionucleoside may be a compound of formula (I) or a tautomer thereof,

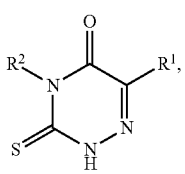

(I)

wherein $R^1$ is hydrogen, alkyl, substituted alkyl, alkyl-aryl, alkyl-heteroaryl, cycloalkyl, aryl, heteroaryl, carboxylic acid, ester, $NR^aR^b$, imine, hydroxyl, or oxo;

$R^2$ is hydrogen, $NR^aR^b$, imine, alkyl, or aryl; and $R^a$ and $R^b$ are each independently hydrogen, alkyl, or aryl.

The thionucleoside may stabilize the luminogenic substrate against decomposition over time, in the presence of light, in the absence of light, and/or at different temperatures. The thionucleoside may stabilize the luminogenic substrate against decomposition into one or more decomposition products over time, in the presence of light, in the absence of light, and/or at different temperatures.

As such, inclusion of the thionucleoside in the composition may stabilize the luminogenic substrate against decomposition by suppressing or reducing the formation of the one or more decomposition products as compared to a composition that does not include the thionucleoside. This, in turn, provides the capability of storing or incubating the luminogenic substrate for a period of time at a particular temperature, in the presence of light, and/or in the absence of light without significant decomposition of the luminogenic substrate before use of the luminogenic substrate in an assay.

The present invention also relates to a method for stabilizing the luminogenic substrate. Such a method may stabilize the luminogenic substrate against decomposition and/or suppress or reduce the formation of the one or more decomposition products. The method may include contacting the luminogenic substrate with an effective amount of the thionucleoside (e.g., 225 mM) in the presence of the organic solvent. This contacting step may include forming the composition described above.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "alkyl" refers to a linear or branched hydrocarbon radical, preferably having 1 to 30 carbon atoms, 1 to 10 carbon atoms, 1 to 6 carbon atoms or 1 to 4 carbon atoms. The term "$C_1$-$C_4$-alkyl" is defined to include alkyl groups having 1, 2, 3, or 4 carbons in a linear or branched arrangement. For example, "$C_1$-$C_4$-alkyl" specifically includes methyl, ethyl, n-propyl, i-propyl, n-butyl, t-butyl, and i-butyl. The term "$C_1$-$C_6$-alkyl" is defined to include alkyl groups having 1, 2, 3, 4, 5 or 6 carbons in a linear or branched arrangement. For example, "$C_1$-$C_6$-alkyl" specifically includes methyl, ethyl, n-propyl, i-propyl, n-butyl, t-butyl, i-butyl, pentyl and hexyl. Alkyl groups of the present invention may be unsubstituted or substituted by one or more suitable substituents, preferably 1 to 3 suitable substituents, as defined herein.

As used herein, the term "alkyl-aryl" refers to an aryl group, as defined herein, appended to the parent molecular moiety through an alkyl group, as defined herein. In some embodiments, the alkyl group may be $C_1$-$C_4$-alkyl.

As used herein, the term "alkyl-heteroaryl" refers to a heteroaryl group, as defined herein, appended to the parent molecular moiety through an alkyl group, as defined here. In some embodiments, the alkyl group may be $C_1$-$C_4$-alkyl.

As used herein, the term "cycloalkyl" refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

As used herein, the term "aryl" refers to monocyclic, bicyclic, or tricyclic aromatic radicals. Representative examples of the aryl groups include, but are not limited to, phenyl, dihydroindenyl, indenyl, naphthyl, dihydronaphthalenyl, and tetrahydronaphthalenyl. Aryl groups of the present invention may be optionally substituted by one or more suitable substituents, preferably 1 to 5 suitable substituents, as defined herein.

As used herein, the term "carboxylic acid" refers to COOH.

As used herein, the term "effective amount" refers to an amount of a thionucleoside, as described herein, for periods of time necessary, to achieve the desired stabilization of a luminogenic substrate, as described herein, against decomposition into one or more decomposition products or degradants.

As used herein, the term "ester" refers to $CO_2R^c$, wherein $R^c$ is alkyl or aryl.

As used herein, the term "heteroaryl" refers to a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl includes a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinazolinyl, quinolinyl, thiazolo[5,4-b]pyridin-2-yl, thiazolo[5,4-d]pyrimidin-2-yl, and 5,6,7,8-tetrahydroquinolin-5-yl. Heteroaryl groups of the present invention may be unsubstituted or substituted by one or more suitable substituents, preferably 1 to 5 suitable substituents, as defined herein.

As used herein, the term "imine" refers to $-N=CR^d$, wherein $R^d$ is alkyl, aryl, heteroaryl, or cycloalkyl, as defined herein. $R^d$ may be unsubstituted or substituted by one or more suitable substituents, as defined herein.

As used herein, the term "hydroxy" refers to an —OH group.

As used herein, the term "oxo" refers to a double-bonded oxygen (=O) radical wherein the bond partner is a carbon atom. Such a radical can also be thought as a carbonyl group.

As used herein, the term "suitable substituent" is intended to mean a chemically acceptable functional group e.g., a moiety that does not negate the activity of the inventive compounds. Illustrative examples of suitable substituents include, but are not limited to, halo groups, perfluoroalkyl groups, perfluoroalkoxy groups, alkyl groups, alkenyl groups, alkynyl groups, hydroxy groups, halo groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. The substituents can be substituted by additional substituents.

If substituents are described as being "independently selected" from a group, each substituent is selected independent of the other. Each substituent, therefore, may be identical to or different from the other substituent(s).

As used herein, the term "light" may refer to visible light, white light (which may be a combination of the three primary colors red light, blue light, and yellow light), violet light, blue light, blue-green light, green light, yellow-green light, yellow light, orange light, red light, or near ultraviolet light, or any combination thereof. The term "light" may refer to light from a region of the electromagnetic spectrum, for example, but not limited to, the visible light region. The term "light" may also refer to light having a wavelength of about 380 nm to about 780 nm, or about 400 nm to about 700 nm. The term "light" may further refer to light from a fluorescent light bulb, a light-emitting diode (LED) bulb, an incandescent light bulb, or any combination thereof. In some embodiments, dark may be an absence of light.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Composition

The present invention is directed to a composition comprising a luminogenic substrate, a thionucleoside, and an organic solvent. The composition does not contain a luminogenic enzyme. The composition may stabilize the luminogenic substrate against decomposition. The composition may stabilize the luminogenic substrate against decomposition as compared to a composition that does not contain the thionucleoside. The thionucleoside may reduce or suppress the formation of one or more decomposition products from the luminogenic substrate.

The composition may stabilize the luminogenic substrate against decomposition in the absence of light (i.e., in the dark). The composition may increase a half-life of the luminogenic substrate in the absence of light as compared to a composition that does not contain the thionucleoside.

The composition may stabilize the luminogenic substrate against decomposition in the presence of light. The composition may increase a half-life of the luminogenic substrate in the presence of light as compared to a composition that does not contain the thionucleoside. The composition may increase the half-life of the luminogenic substrate in the presence of light about 1.1-fold, 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold, 3.5-fold, 3.6-fold, 3.7-fold, 3.8-fold, 3.9-fold, 4.0-fold, 4.1-fold, 4.2-fold, 4.3-fold, 4.4-fold, 4.5-fold, 4.6-fold, 4.7-fold, 4.8-fold, 4.9-fold, or 5.0-fold as compared to the composition that does not contain the thionucleoside.

The composition may stabilize the luminogenic substrate against decomposition at temperatures from about −120° C. to about 80° C., about −110° C. to about 80° C., about −100° C. to about 80° C., about −90° C. to about 80° C., about −85° C. to about 80° C., about −80° C. to about 80° C., about −75° C. to about 80° C., about −70° C. to about 80° C., about −65° C. to about 80° C., about −60° C. to about 80° C., about −55° C. to about 80° C., about −50° C. to about 80° C., about −45° C. to about 80° C., about −40° C. to about 80° C., about −35° C. to about 80° C., about −30° C. to about 80° C., about −25° C. to about 80° C., about −20° C. to about 80° C., about −15° C. to about 80° C., about −10° C. to about 80° C., about −5° C. to about 80° C., about 0° C. to about 80° C., about −120° C. to about 75° C., about −120° C. to about 70° C., about −120° C. to about 65° C., about −120° C. to about 60° C., about −120° C. to about 55° C., about −120° C. to about 50° C., about −120° C. to about 45° C., about −120° C. to about 40° C., about −120° C. to about 35° C., about −120° C. to about 30° C., about −120° C. to about 25° C., about −120° C. to about 20° C., about −100° C. to about 70° C., about −80° C. to about 60° C., about −80° C. to about 55° C., about −80° C. to about 50° C., about −80° C. to about 45° C., about −80° C. to about 40° C., about −80° C. to about 35° C., about −80° C. to about 30° C., about −80° C. to about 25° C., about −20° C. to about 60° C., about −20° C. to about 55° C., about −20 to about 50° C., about −20° C. to about 45° C., about −20° C. to about 40° C., about −20° C. to about 35° C., about −20° C. to about 30° C., or about −20° C. to about 25° C.

The composition may stabilize the luminogenic substrate against decomposition at about −120° C., −115° C., −110° C., −105° C., −100° C., −95° C., −90° C., −89° C., −88° C., −87° C., −86° C., −85° C., −84° C., −83° C., −82° C., −81° C., −80° C., −79° C., −78° C., −77° C., −76° C., −75° C., −74° C., −73° C., −72° C., −71° C., −70° C., −69° C., −68° C., −67° C., −66° C., −65° C., −64° C., −63° C., −62° C., −61° C., −60° C., −59° C., −58° C., −57° C., −56° C., −55° C., −54° C., −53° C., −52° C., −51° C., −50° C., −49° C., −48° C., −47° C., −46° C., −45° C., −44° C., −43° C., −42° C., −41° C., −40° C., −39° C., −38° C., −37° C., −36° C., −35° C., −34° C., −33° C., −32° C., −31° C., −30° C., −29° C., −28° C., −27° C., −26° C., −25° C., −24° C., −23° C., −22° C., −21° C., −20° C., −19° C., −18° C., −17° C., −16° C., −15° C., −14° C., −13° C., −12° C., −11° C., −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 75° C., or 80° C. The composition may stabilize the luminogenic substrate against decomposition at about −80° C., about −20° C., about 4° C., or about 20° C.

The composition may stabilize the luminogenic substrate against decomposition for at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 35 days, 40 days, 45 days, 50 days, 55 days, 60 days, 65 days, 70 days, 75 days, 80 days, 85 days, 90 days, 100 days, 110 days, 120 days, 130 days, 140 days, 150 days, 160 days, 170 days, 180 days, 190 days, 200 days, 210 days, 220 days, 230 days, 240 days, 250 days, 260 days, 270 days, 280 days, 290 days, 300 days, 310 days, 320 days, 330 days, 340 days, 350 days, 360 days, 1 year, 2 years, 3 years, 4 years, or 5 years.

The composition may increase the half-life of the luminogenic substrate by at least about 1.25-fold, 1.5-fold, 1.75-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, or 25-fold as compared to the composition that does not include the thionucleoside.

a. Luminogenic Substrate

The composition includes the luminogenic substrate. The luminogenic substrate may be a molecule capable of creating light via a chemical reaction. The luminogenic substrate may be coelenterazine, coelenterazine-h, coelenterazine-h-h, furimazine, a functional analog thereof, a derivative thereof, or any combination thereof. The luminogenic substrate may be one or more compounds disclosed in U.S. Pat. No. 8,809,529 and U.S. Patent Application Publication No. 2015/0064731, the entire contents of both of which are incorporated herein by reference.

As described above, the composition stabilizes the luminogenic substrate against decomposition. The luminogenic substrate may be stabilized against decomposition by the thionucleoside, which is described below in more detail. The luminogenic substrate may be stabilized against decomposition to one or more decomposition products by the thionucleoside.

The thionucleoside may stabilize the luminogenic substrate against decomposition in the presence of light, in the absence of light, and/or at different temperatures as described above.

The luminogenic substrate may be present in the composition at about 0.5 mM to about 10 mM, about 0.75 mM to about 10 mM, about 1.0 mM to about 10 mM, about 0.5 mM to about 9 mM, about 0.5 mM to about 8 mM, about 0.5 mM to about 7 mM, about 0.5 mM to about 6 mM, about 0.5 mM to about 5 mM, about 0.5 mM to about 4 mM, about 0.5 mM to about 3 mM, or about 0.5 mM to about 2 mM. The luminogenic substrate may be present in the composition at about 0.5 mM, 0.6 mM, 0.7 mM, 0.8 mM, 0.9 mM, 1.0 mM, 1.1 mM, 1.2 mM, 1.25 mM, 1.3 mM, 1.4 mM, 1.5 mM, 1.6 mM, 1.7 mM, 1.8 mM, 1.9 mM, 2 mM, 2.5 mM, 3 mM, 3.5 mM, 4 mM, 4.5 mM, 5 mM, 5.5 mM, 6 mM, 6.5 mM, 7 mM, 7.5 mM, 8 mM, 8.5 mM, 9 mM, 9.5 mM, or 10 mM.

(1) Coelenterazine

The luminogenic substrate may be coelenterazine, a functional analog thereof, a derivative thereof, or any combination thereof. Coelenterazine may have the following structure:

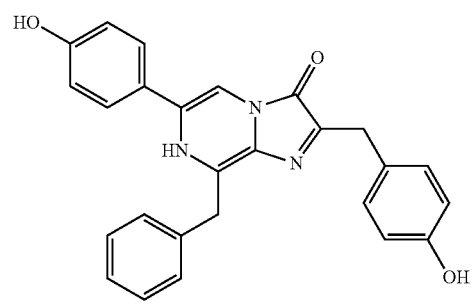 [SMILES: O=c1c(Cc2ccc(O)cc2)nc2c(Cc3ccccc3)[nH]c(-c3ccc(O)cc3)cn1-2]

Coelenterazine may be stabilized against decomposition by the thionucleoside described below. The thionucleoside may reduce or suppress the formation of one or more decomposition products from coelenterazine.

(2) Coelenterazine-h

The luminogenic substrate may be coelenterazine-h, a functional analog thereof, a derivative thereof, or any combination thereof. Coelenterazine-h may have the following structure:

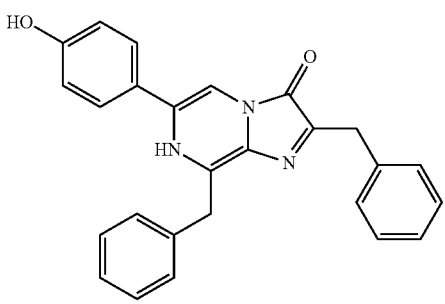 [SMILES: O=c1c(Cc2ccccc2)nc2c(Cc3ccccc3)[nH]c(-c3ccc(O)cc3)cn1-2]

Coelenterazine-h may be stabilized against decomposition by the thionucleoside described below. The thionucleoside may reduce or suppress the formation of one or more decomposition products from coelenterazine-h.

(3) Coelenterazine-h-h

The luminogenic substrate may be coelenterazine-h-h, a functional analog thereof, a derivative thereof, or any combination thereof. Coelenterazine-h-h may have the following structure:

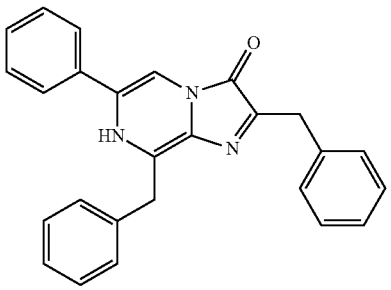 [SMILES: O=c1c(Cc2ccccc2)nc2c(Cc3ccccc3)[nH]c(-c3ccccc3)cn1-2]

Coelenterazine-h-h may be stabilized against decomposition by the thionucleoside described below. The thionucleoside may reduce or suppress the formation of one or more decomposition products from coelenterazine-h-h.

(4) Furimazine

The luminogenic substrate may be furimazine, a functional analog thereof, a derivative thereof, or any combination thereof. Furimazine may have the following structure:

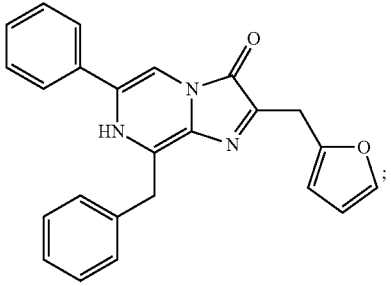 [SMILES: O=c1c(Cc2ccco2)nc2c(Cc3ccccc3)[nH]c(-c3ccccc3)cn1-2]

Furimazine may be stabilized against decomposition by the thionucleoside described below. The thionucleoside may reduce or suppress the formation of one or more decomposition products from furimazine.

b. Thionucleoside

The composition may include the thionucleoside. The thionucleoside may stabilize the luminogenic substrate against decomposition into one or more decomposition products. The thionucleoside may reduce or suppress the formation of the one or more decomposition products. Such stabilization, reduction, or suppression may be in the presence of light, in the absence of light, and/or at different temperatures as described above.

The thionucleoside may be a compound of formula (I) or a tautomer thereof,

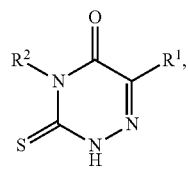

(I)

wherein $R^1$ is hydrogen, alkyl, substituted alkyl, alkyl-aryl, alkyl-heteroaryl, cycloalkyl, aryl, heteroaryl, carboxylic acid, ester, $NR^aR^b$, imine, hydroxyl, or oxo;

$R^2$ is hydrogen, $NR^aR^b$, imine, alkyl, or aryl; and $R^a$ and $R^b$ are each independently hydrogen, alkyl, or aryl.

In certain embodiments, $R^1$ is hydrogen, alkyl, substituted alkyl, alkyl-aryl, alkyl-heteroaryl, cycloalkyl, aryl, heteroaryl, carboxylic acid, ester, $NR^aR^b$, imine, hydroxyl, or oxo; wherein $R^a$ and $R^b$ are each independently hydrogen, alkyl, or aryl; and wherein said alkyl, aryl, heteroaryl, cycloalkyl, alkyl-aryl, alkyl-heteroaryl, and imine, at each occurrence, are independently unsubstituted or substituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, $R^1$ is alkyl, substituted alkyl, alkyl-aryl, alkyl-heteroaryl, cycloalkyl, carboxylic acid, ester, or oxo; wherein said alkyl, cycloalkyl, and alkyl-aryl, at each occurrence, are independently unsubstituted or substituted with 1, 2, or 3 functional groups independently selected from the group consisting of halogen, nitro, hydroxy, amino, alkylamino, and —COOH.

In certain embodiments, $R^2$ is hydrogen, $NR^aR^b$, imine, alkyl, or aryl; wherein $R^a$ and $R^b$ are each independently hydrogen, alkyl, or aryl; wherein said alkyl, imine, and aryl, at each occurrence, are independently unsubstituted or substituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, $R^2$ is hydrogen, $NR^aR^b$, or imine; wherein $R^a$ and $R^b$ are each independently hydrogen or alkyl; wherein said imine is unsubstituted or substituted with a functional group independently selected from the group consisting of halogen, nitro, hydroxy, amino, and alkylamino.

In certain embodiments, $R^2$ is imine; wherein imine is —N=$CR^d$; wherein $R^d$ is alkyl, aryl, heteroaryl, or cycloalkyl; wherein said imine is unsubstituted or substituted with a functional group independently selected from the group consisting of halogen, nitro, hydroxy, amino, and alkylamino.

In certain embodiments. $R^2$ is imine; wherein imine is —N=$CR^d$; wherein $R^d$ is aryl or heteroaryl; wherein said imine is unsubstituted or substituted with a functional group independently selected from the group consisting of nitro and alkylamino.

The compound of formula (I) may be ATT (6-methyl-3-thioxo-3,4-dihydro-1,2,4-triazin-5(2H)-one), which has the following structure:

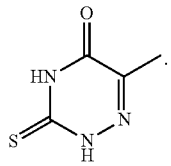

ATT may also be known as 6-Aza-2-thiothymine. ATT is commercially available, for example, from Sigma-Aldrich (catalog number 275514).

The compound of formula (I) may be ATCA (5-oxo-3-thioxo-2,3,4,5-tetrahydro-1,2,4-triazine-6-carboxylic acid), which has the following structure:

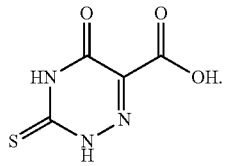 [SMILES: O=C(O)c1n[nH]c(=S)[nH]c1=O]

ATCA is commercially available, for example, from Sigma-Aldrich (catalog number S784028).

The compound of formula (I) may be 3-(4-Amino-5-oxo-3-thioxo-2,3,4,5-tetrahydro-1,2,4-triazin-6-yl)propanoic acid, which has the following structure:

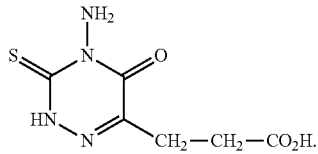 [SMILES: Nn1c(=S)[nH]nc(CCC(=O)O)c1=O]

This compound is commercially available, for example, from Sigma-Aldrich (catalog number OTV000379.

The compound of formula (I) may be tetrahydro-2-methyl-3-thioxo-1,2,4-triazine-5,6-dione, which has the following structure:

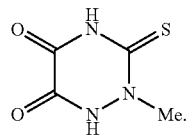

This compound may also be known as thiotriazinone and is commercially available, for example, from Sigma Aldrich (catalog number 549756).

The compound of formula (I) may be 4-((2-furylmethylene)amino)-3-mercapto-6-methyl-1,2,4-triazin-5(4H)-one, which has the following structure:

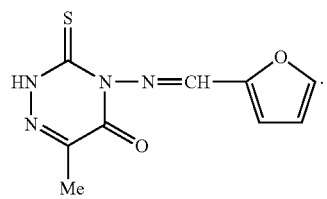 [SMILES: Cc1n[nH]c(=S)n(N=Cc2ccco2)c1=O]

This compound is commercially available, for example, from Sigma Aldrich (catalog number L125016).

The compound of formula (I) may be 6-benzyl-3-sulfanyl-1,2,4-triazin-5-ol, which has the following structure:

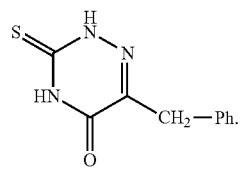 [SMILES: O=c1[nH]c(=S)[nH]nc1Cc1ccccc1]

This compound may also be known as b-ATT, benzyl-ATT, or TAK-0002.

The compound of formula (I) may be 4-amino-3-mercapto-6-methyl-1,2,4-triazin-5(4H)-one, which has the following structure:

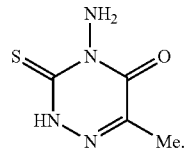

This compound is commercially available, for example, from Sigma-Aldrich (catalog number PH125903).

The compound of formula (I) may be 3-(5-oxo-3-thioxo-2,3,4,5-tetrahydro-1,2,4-triazin-6-yl)propanoic acid, which has the following structure:

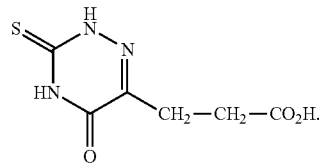 [SMILES: O=C(O)CCc1n[nH]c(=S)[nH]c1=O]

This compound is commercially available, for example, from Sigma-Aldrich (catalog number L151629).

The compound of formula (I) may be (E)-6-methyl-4-((thiophen-2-ylmethylene)amino)-3-thioxo-3,4-dihydro-1,2,4-triazin-5(2H)-one, which has the following structure:

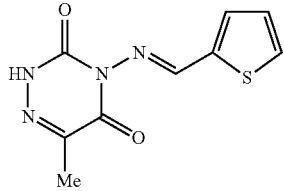 [SMILES: Cc1n[nH]c(=O)n(/N=C/c2cccs2)c1=O]

This compound is commercially available, for example, from Sigma Aldrich (catalog number L150819).

The compound of formula (I) may be (E)-6-methyl-4-((3-nitrobenzylidene)amino)-3-thioxo-3,4-dihydro-1,2,4-triazin-5(2H)-one, which has the following structure:

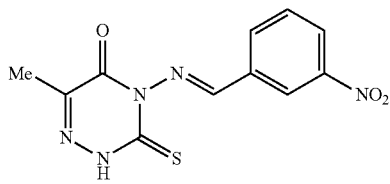 [SMILES: Cc1n[nH]c(=S)n(/N=C/c2cccc([N+](=O)[O-])c2)c1=O]

This compound is commercially available, for example, from Sigma Aldrich (catalog number L151238).

The compound of formula (I) may be (E)-4-((4-(diethylamino)benzylidene)amino)-6-methyl-3-thioxo-3,4-dihydro-1,2,4-triazin-5(2H)-one, which has the following structure:

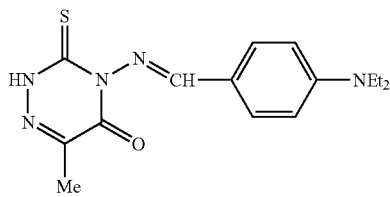

This compound is commercially available, for example, from Sigma Aldrich (catalog number L151211).

The compound of formula (I) may be ATCA ethyl ester, which has the following structure:

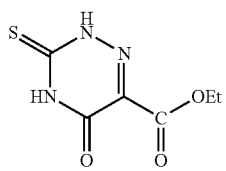 [SMILES: CCOC(=O)c1n[nH]c(=S)[nH]c1=O]

This compound is commercially available, for example, from Sigma Aldrich (catalog number PH008592).

The compound of formula (I) may be TAK-0021, which has the following structure:

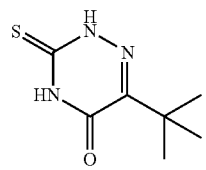

The compound of formula (I) may be TAK-0020, which has the following structure:

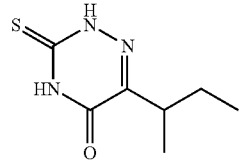

The compound of formula (I) may be TAK-0018, which has the following structure:

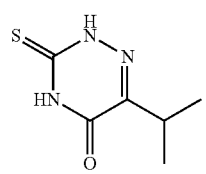

The compound of formula (I) may be TAK-0009, which has the following structure:

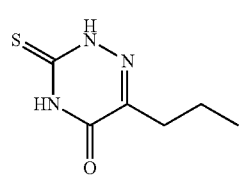

The compound of formula (I) may be TAK-0014, which has the following structure:

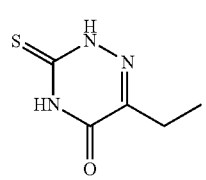

The compound of formula (I) may be TAK-0007, which has the following structure:

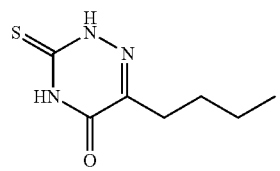

The compound of formula (I) may be TAK-0008, which has the following structure:

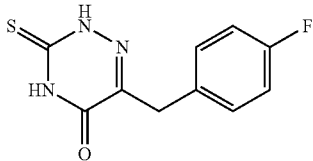 [SMILES: O=c1[nH]c(=S)[nH]nc1Cc1ccc(F)cc1]

The compound of formula (I) may be TAK-0003, which has the following structure:

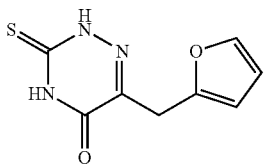 [SMILES: O=c1[nH]c(=S)[nH]nc1Cc1ccco1]

The compound of formula (I) may be TAK-0004, which has the following structure:

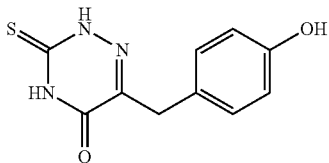 [SMILES: O=c1[nH]c(=S)[nH]nc1Cc1ccc(O)cc1]

The compound of formula (I) may be 3-thioxo-6-(trifluoromethyl)-3,4-dihydro-1,2,4-triazin-5(2H)-one, which has the following structure:

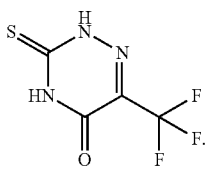 [SMILES: O=c1[nH]c(=S)[nH]nc1C(F)(F)F]

The compound of formula (I) may be 6-cyclopropyl-3-thioxo-3,4-dihydro-1,2,4-triazin-5(2H)-one, which has the following structure:

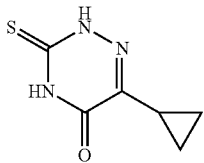 [SMILES: O=c1[nH]c(=S)[nH]nc1C1CC1]

The compound of formula (I) may be 6-(hydroxymethyl)-3-thioxo-3,4-dihydro-1,2,4-triazin-5(2H)-one, which has the following structure:

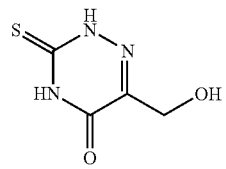

TAK-0014, TAK-0002, TAK-0021, TAK-0020, TAK-0018, TAK-0009, TAK-0007, TAK-0008, TAK-0003, TAK-0004, 3-thioxo-6-(trifluoromethyl)-3,4-dihydro-1,2,4-triazin-5(2H)-one, 6-cyclopropyl-3-thioxo-3,4-dihydro-1,2,4-triazin-5(2H)-one, and 6-(hydroxymethyl)-3-thioxo-3,4-dihydro-1,2,4-triazin-5(2H)-one were synthesized as described in S. J. Liu et al., ARKIVOC (2009) 333-348 and S. J. Liu et al., Letters in Drug Design and Discovery (2010) 7:5-8, the entire contents of both of which are herein incorporated by reference.

The thionucleoside may be present in the composition at an amount effective to stabilize the luminogenic substrate against decomposition. The effective amount of the thionucleoside in the composition to stabilize the luminogenic substrate against decomposition may be about 0.1 mM to about 500 mM, about 0.5 mM to about 500 mM, about 1 mM to about 500 mM, about 5 mM to about 500 mM, about 10 mM to about 500 mM, about 15 mM to about 500 mM, about 20 mM to about 500 mM, about 30 mM to about 500 mM, about 50 mM to about 500 nM, about 70 mM to about 500 mM, about 90 mM to about 500 mM, about 110 mM to about 500 mM, about 130 mM to about 500 mM, about 150 mM to about 500 mM, about 170 mM to about 500 mM, about 190 mM to about 500 mM, about 210 mM to about 500 mM, about 0.1 mM to about 475 mM, about 0.1 mM to about 450 mM, about 0.1 mM to about 425 mM, about 0.1 mM to about 400 mM, about 0.1 mM to about 375 mM, about 0.1 mM to about 350 mM, about 0.1 mM to about 325 mM, about 0.1 mM to about 300 mM, about 0.1 mM to about 275 mM, about 0.5 mM to about 450 mM, about 1 mM to about 400 mM, about 2 mM to about 350 mM, about 3 mM to about 300 mM, about 4 mM to about 300 mM, or about 5 mM to about 250 mM.

The effective amount of the thionucleoside in the composition to stabilize the luminogenic substrate against decomposition may be about 0.1 mM, 0.2 mM, 0.3 mM, 0.4 mM, 0.5 mM, 0.6 mM, 0.7 mM, 0.8 mM, 0.9 mM, 1.0 mM, 1.5 mM, 2.0 mM, 2.5 mM, 3.0 mM, 3.5 mM, 4.0 mM, 4.5 mM, 5.0 mM, 5.5 mM, 6.0 mM, 6.5 mM, 7.0 mM, 7.5 mM, 8.0 mM, 8.5 mM, 9.0 mM, 9.5 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, 50 mM, 51 mM, 52 mM, 53 mM, 54 mM, 55 mM, 56 mM, 57 mM, 58 mM, 59 mM, 60 mM, 61 mM, 62 mM, 63 mM, 64 mM, 65 mM, 66 mM, 67 mM, 68 mM, 69 mM, 70 mM, 71 mM, 72 mM, 73 mM, 74 mM, 75 mM, 76 mM, 77 mM, 78 mM, 79 mM, 80 mM, 81 mM, 82 mM, 83 mM, 84 mM, 85 mM, 86 mM, 87 mM, 88 mM, 89 mM, 90 mM, 91 mM, 92 mM, 93 mM, 94 mM, 95 mM, 96 mM, 97 mM, 98 mM, 99 mM, 100 mM, 105 mM, 110 mM, 115 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, 200 mM, 205 mM, 210 mM, 215 mM, 220 mM, 225 mM, 230 mM, 235 mM, 240 mM, 245 mM, 250 mM, 255 mM, 260 mM, 265 mM, 270 mM, 275 mM, 280 mM, 285 mM, 290 mM, 295 mM, 300 mM, 305 mM, 310 mM, 315 mM, 320 mM, 325 mM, 330 mM, 335 mM, 340 mM, 345 mM, 350 mM, 355 mM, 360 mM, 365 mM, 370 mM, 375 mM, 380 mM, 385 mM, 390 mM, 395 mM, 400 mM, 405 mM, 410 mM, 415 mM, 420 mM, 425 mM, 430 mM, 435 mM, 440 mM, 445 mM, 450 mM, 455 mM, 460 mM, 465 mM, 470 mM, 475 mM, 480 mM, 485 mM, 490 mM, 495 mM, or 500 mM.

The effective amount of the thionucleoside in the composition to stabilize the luminogenic substrate against decomposition may be greater than 0.1 mM, 0.5 mM, or 1 mM.

In some embodiments, when the thionucleoside is ATT, the effective amount of ATT to stabilize the luminogenic substrate against decomposition may be about 90 mM to about 500 mM, about 100 mM to about 500 mM, about 110 mM to about 500 mM, about 120 mM to about 500 mM, about 130 mM to about 500 mM, about 140 mM to about 500 mM, about 150 mM to about 500 mM, about 160 mM to about 500 mM, about 170 mM to about 500 mM, about 180 mM to about 500 mM, about 190 mM to about 500 mM, about 200 mM to about 500 mM, about 210 mM to about 500 mM, about 90 mM to about 475 mM, about 90 mM to about 450 mM, about 90 mM to about 425 mM, about 90 mM to about 400 mM, about 90 mM to about 375 mM, about 90 mM to about 350 mM, about 90 mM to about 325 mM, about 90 mM to about 300 mM, about 90 mM to about 275 mM, about 100 mM to about 450 mM, about 125 mM to about 400 mM, about 175 mM to about 350 mM, or about 200 mM to about 300 mM.

In other embodiments, when the thionucleoside is ATT, the effective amount of ATT to stabilize the luminogenic substrate against decomposition may be about 90 mM, 91 mM, 92 mM, 93 mM, 94 mM, 95 mM, 96 mM, 97 mM, 98 mM, 99 mM, 100 mM, 105 mM, 110 mM, 115 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, 200 mM, 201 mM, 202 mM, 203 mM, 204 mM, 205 mM, 206 mM, 207 mM, 208 mM, 209 mM, 210 mM, 211 mM, 212 mM, 213 mM, 214 mM, 215 mM, 216 mM, 217 mM, 218 mM, 219 mM, 220 mM, 221 mM, 222 mM, 223 mM, 224 mM, 225 mM, 226 mM, 227 mM, 228 mM, 229 mM, 230 mM, 231 mM, 232 mM, 233 mM, 234 mM, 235 mM, 236 mM, 237 mM, 238 mM, 239 mM, 240 mM, 241 mM, 242 mM, 243 mM, 244 mM, 245 mM, 246 mM, 247 mM, 248 mM, 249 mM, 250 mM, 251 mM, 252 mM, 253 mM, 245 mM, 255 mM, 256 mM, 257 mM, 258 mM, 259 mM, 260 mM, 261 mM, 262 mM, 263 mM, 264 mM, 265 mM, 266 mM, 267 mM, 268 mM, 269 mM, 270 mM, 271 mM, 272 mM, 273 mM, 274 mM, 275 mM, 276 mM, 277 mM, 278 mM, 279 mM, 280 mM, 281 mM, 282 mM, 283 mM, 284 mM, 285 mM, 286 mM, 287 mM, 288 mM, 289 mM, 290 mM, 291 mM, 292 mM, 293 mM, 294 mM, 295 mM, 296 mM, 297 mM, 298 mM, 299 mM, 300 mM, 305 mM, 310 mM, 315 mM, 320 mM, 325 mM, 330 mM, 335 mM, 340 mM, 345 mM, 350 mM, 355 mM, 360 mM, 365 mM, 370 mM, 375 mM, 380 mM, 385 mM, 390 mM, 395 mM, 400 mM, 405 mM, 410 mM, 415 mM, 420 mM, 425 mM, 430 mM, 435 mM, 440 mM, 445 mM, 450 mM, 455 mM, 460 mM, 465 mM, 470 mM, 475 mM, 480 mM, 485 mM, 490 mM, 495 mM, or 500 mM.

In still other embodiment, when the thionucleoside is ATT, the effective amount of ATT to stabilize the luminogenic substrate against decomposition may be 225 mM. In other embodiments, when the thionucleoside is ATT, the effective amount of ATT to stabilize the luminogenic substrate against decomposition may be greater than about 32 mM, greater than about 50 mM, or greater than about 100 mM.

c. Organic Solvent

The composition may include the organic solvent. The organic solvent may be alcohol, propylene glycol, dimethyl sulfoxide (DMSO), acetonitrile, glycerol, or any combination thereof. The alcohol may be ethanol.

In some embodiments, the organic solvent may be a combination of alcohol and propylene glycol. In other embodiments, the organic solvent may be a combination of ethanol and propylene glycol. In still other embodiments, the organic solvent may be a ratio of 1:1 of ethanol:propylene glycol (e.g., 50% (v/v) ethanol:50% (v/v) propylene glycol). In another embodiment, the organic solvent may be 40% (v/v) ethanol:60% (v/v) propylene glycol.

In some embodiments, the organic solvent may be a combination of alcohol and glycerol. In other embodiments, the organic solvent may be a combination of ethanol and glycerol. In still other embodiments, the organic solvent may be 85% (v/v) ethanol:15% (v/v) glycerol.

d. Luminogenic Enzyme

As described above, the composition may not include a luminogenic enzyme, a variant thereof, a mutant thereof, or any combination thereof. The luminogenic enzyme may be naturally occurring, recombinant, or mutant. The luminogenic enzyme may use the luminogenic substrate described above (including derivatives or analogs thereof) as a substrate to catalyze a reaction the produces light or that leads to the production of light.

The luminogenic enzyme may include a luciferase derived from *Vargula higendorfli*, bioluminescent decapods, such as from the Oplophoroidea, e.g. *Oplophorus*-derived luciferases, bioluminescent copepods such as *Gaussia princeps* and *Metridia longa*, marine organisms such as cnidarians (e.g., *Renilla* luciferase), Aristeidae, Solenoceridae, Luciferidae, Sergestidae, Pasipheidae and Thalassocarididae decapoda families, and photoproteins, such as Aequorin, and variants and mutants of said luciferases.

3. Method of Stabilization

Also provided herein is a method for stabilizing the luminogenic substrate. The method may stabilize the luminogenic substrate against decomposition. The method may stabilize the luminogenic substrate against decomposition to one or more decomposition products.

The method may include contacting the luminogenic substrate with the effective amount of the thionucleoside in the presence of the organic solvent. Effective amounts of the thionucleoside, which stabilize the luminogenic substrate against decomposition, are described above. Accordingly, the contacting step may include forming the composition described above, thereby stabilizing the luminogenic substrate against decomposition.

4. Kit

Also provided herein is a kit that includes the composition described above. The composition may be contained within a single container.

The kit according to the present disclosure preferably includes instructions for storing the composition and/or the single container containing the composition. Instructions included in the kit of the present disclosure may be affixed to packaging material or may be included as a package insert. While instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site which provides instructions.

The present invention has multiple aspects, illustrated by the following non-limiting examples.

5. Examples

Example 1

Stability of Coelenterazine

The stability of coelenterazine in the presence and absence of ATT was measured over time at different temperatures. Specifically, 1.25 mM coelenterazine was present in a solution of 50% ethanol and 50% propylene glycol (i.e., the solution without ATT) or a solution of 50% ethanol and 50% propylene glycol with 225 mM ATT (i.e., the solution with ATT). These two solutions were incubated at −20° C., room temperature (RT), 40° C., or 60° C. and analyzed at 0 days, 1 day, 3 days, 7 days, 15 days, and 30 days.

Following incubation, high performance liquid chromatography (HPLC) was utilized to identify the components of the respective solutions at each time point. Specifically, an Agilent 1100 HPLC instrument was used and equipped with a quaternary pump, thermostatted autosampler and column compartment, and a G1311B diode-array detector. The column used was a Synergi-MAX-RP (Phenomenex, Torrance, Calif.) 100 AÅ 50×4.6 2.5 µm. The run on the HPLC was a gradient run with 0.1% TFA in water and acetonitrile. Absorbance was measured at 262 nanometers (nm). Standards of coelenterazine and its known degradants were run to confirm both the retention time and absorbance trace. 5 µl of each solution was injected and the retention time of coelenterazine was 3.9 minutes at room temperature.

Figure 1B:
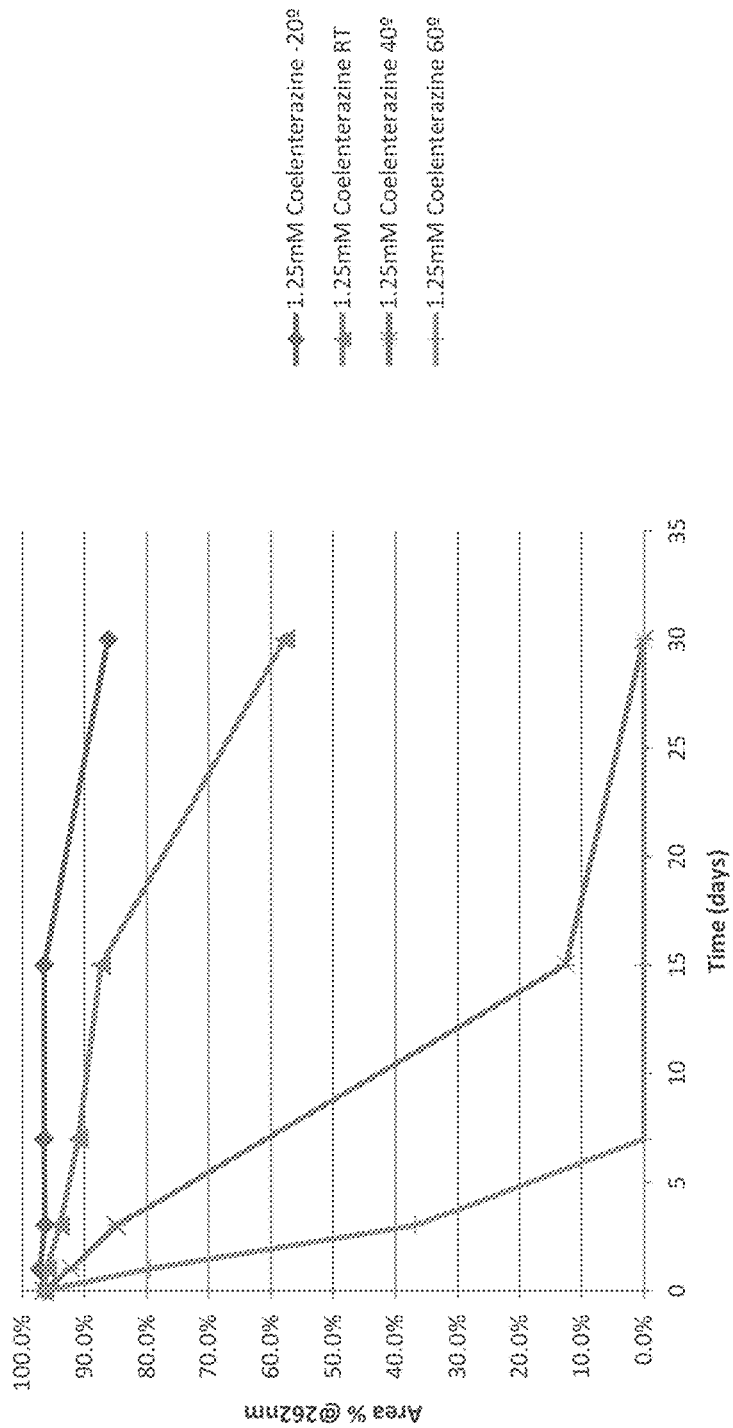
FIG. 1B shows the stability of coelenterazine in the absence of ATT.

The results of the HPLC analysis are shown below in Tables 1 and 2 and FIGS. 1A and 1B, in which the values are reported as relative peak area percentage at 262 nm (i.e., the lamba max of the substrate). FIG. 1A shows the relative peak area percentage of the solution with ATT over time (in days) while FIG. 1B shows the relative peak area percentage of the solution without ATT over time (in days). In each of FIGS. 1A and 1B, diamond is 1.25 mM coelenterazine incubated over time with or without 225 mM ATT, respectively, at −20° C., triangle is 1.25 mM coelenterazine incubated over time with or without 225 mM ATT, respectively, at room temperature (RT), star is 1.25 mM coelenterazine incubated over time with or without 225 mM ATT, respectively, at 40° C., and cross is 1.25 mM coelenterazine incubated over time with or without 225 mM ATT, respectively, at 60° C.

TABLE 1

| | Temperature (in Celsius) | | | |
| --- | --- | --- | --- | --- |
| | −20° | | RT | |
| Time (days) | 1.25 mM Coelenterazine (27-957-28) with 225 mM ATT | 1.25 mM Coelenterazine (27-957-28) | 1.25 mM Coelenterazine (27-957-28) with 225 mM ATT | 1.25 mM Coelenterazine (27-957-28) |
| 0 | 97.0% | 96.5% | 97.0% | 96.5% |
| 1 | 97.3% | 97.2% | 97.1% | 96.1% |
| 3 | 95.8% | 96.4% | 95.8% | 94.0% |
| 7 | 96.3% | 96.5% | 93.8% | 91.0% |
| 15 | 96.3% | 96.5% | 90.5% | 87.4% |
| 30 | 96.3% | 86.2% | 84.9% | 57.7% |

TABLE 2

| | Temperature (in Celsius) | | | |
| --- | --- | --- | --- | --- |
| | 40° | | 60° | |
| Time (days) | 1.25 mM Coelenterazine (27-957-28) with 225 mM ATT | 1.25 mM Coelenterazine (27-957-28) | 1.25 mM Coelenterazine (27-957-28) with 225 mM ATT | 1.25 mM Coelenterazine (27-957-28) |
| 0 | 97.0% | 96.5% | 97.0% | 96.5% |
| 1 | 96.5% | 92.2% | 91.8% | 79.6% |
| 3 | 92.7% | 84.9% | 68.5% | 36.8% |
| 7 | 85.4% | * | 33.8% | ND |
| 15 | 68.7% | 12.6% | ND | ND |
| 30 | 35.1% | ND** | ND | ND |

* Unable to determine area percent due to co-eluting peaks.
**ND = not determined.

From the HPLC analysis, the half-life of coelenterazine in the presence of ATT at 40° C. and 60° C. was calculated to be 23 days and 5 days, respectively, while the half-life of coelenterazine in the absence of ATT at 40° C. and 60° C. was calculated to be 9.5 days and 2 days, respectively (see Table 3 below).

TABLE 3

| | Estimated from graph | | Calculated from Arrhenius | | |
| --- | --- | --- | --- | --- | --- |
| Temperature | $T_{1/2}$ coel + ATT | $T_{1/2}$ coel no ATT | $T_{1/2}$ coel + ATT | $T_{1/2}$ coel no ATT | Fold Stabilizing |
| −75° C. | | | 5.60E+05 years | 1.70E+05 years | 3.29 |
| −20° C. | | | 42.5 years | 5.3 years | 8.02 |
| 20° C. | | | 147 days | 35.5 days | 4.14 |
| 40° C. | 23 days | 9.5 days | 22.3 days | 7.1 days | 3.14 |
| 60° C. | 5 days | 2 days | 4.3 days | 1.7 days | 2.53 |

Additionally, Arrhenius plots were generated for coelenterazine in the presence and absence of ATT to calculate the half-life of coelenterazine at various temperatures. The Arrhenius equation is as follows:

$$k = Ae^{\frac{-E_a}{RT}}.$$

The transformed equation is as follows:

$$\ln(k) = \ln(A) - \frac{E_a}{R} \cdot \frac{1}{T}.$$

Figure 7:
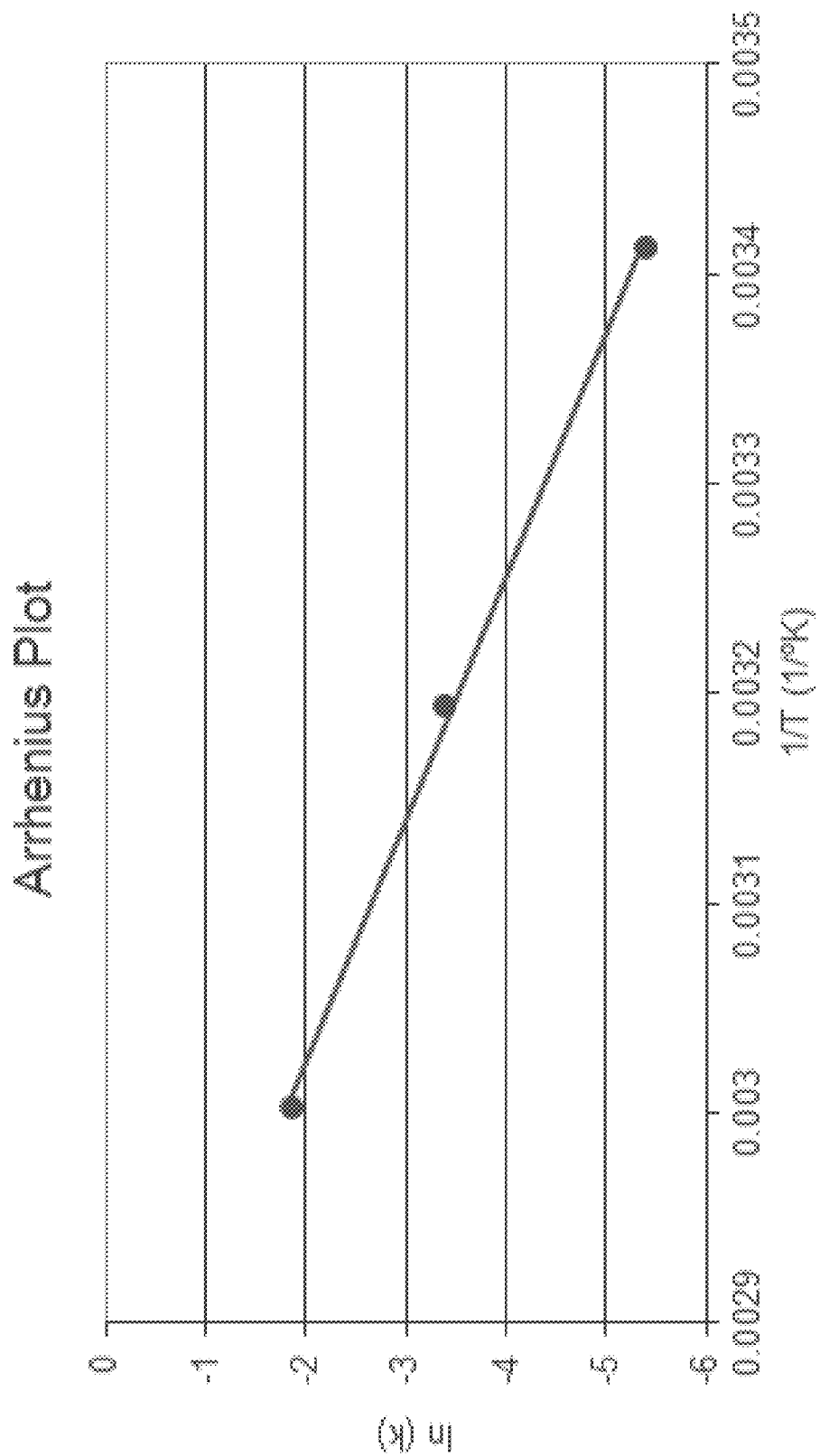
FIG. 7 shows an Arrhenius plot for coelenterazine in the presence of ATT.

The Arrhenius plot for coelenterazine in the presence of ATT is shown in FIG. 7. In FIG. 7, the slope was −8636.59, the intercept was 24.1199, and $R^2$ was 0.9983.

Figure 8:
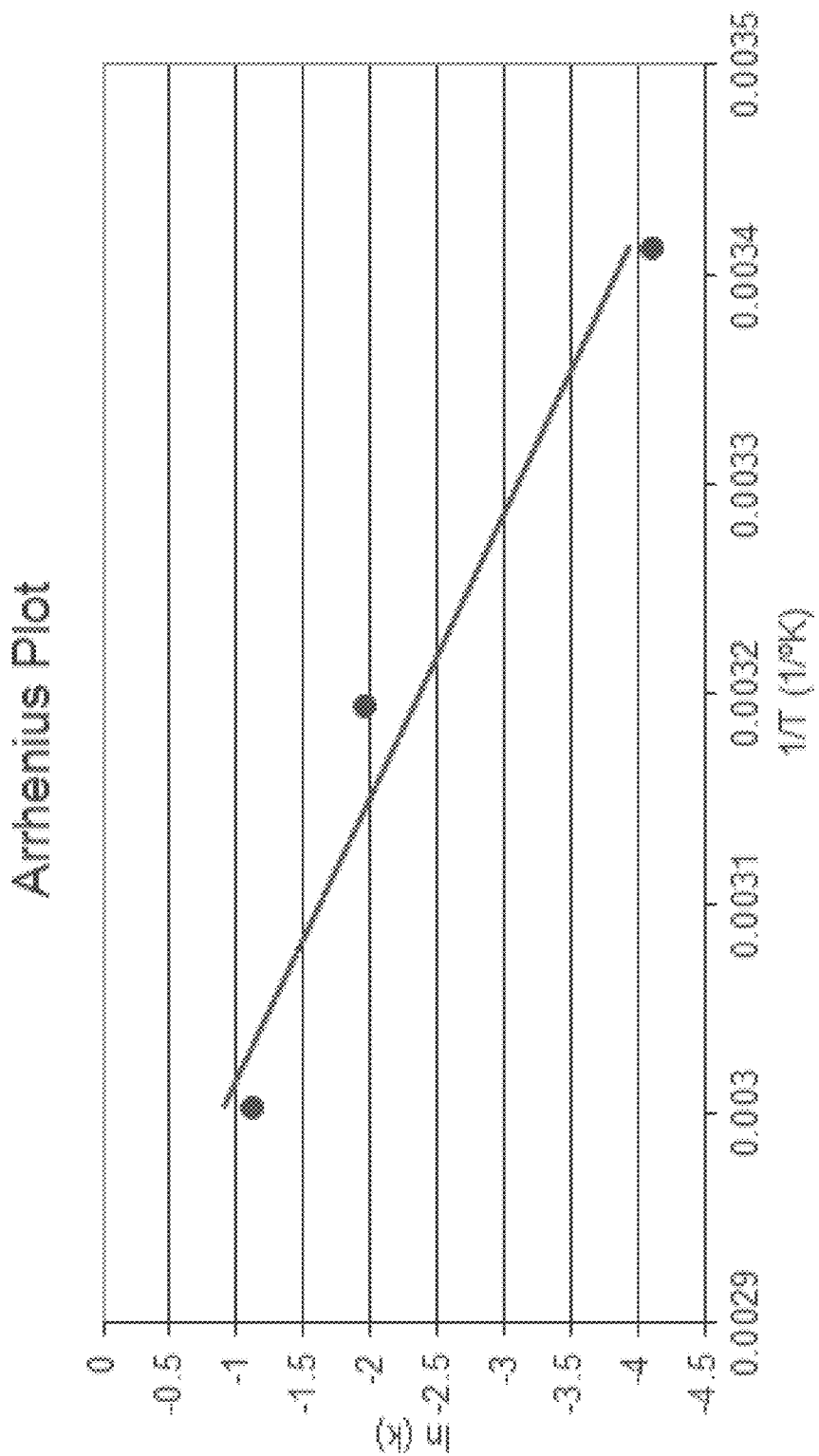
FIG. 8 shows an Arrhenius plot for coelenterazine in the absence of ATT.

The Arrhenius plot for coelenterazine in the absence of ATT is shown in FIG. 8. In FIG. 8, the slope was −7382.51, the intercept was 21.2598, and $R^2$ was 0.9570.

Additionally, the calculated half-lives from the Arrhenius plot indicated that the presence of ATT stabilized coelenterazine against decomposition 3.29-fold, 8.02-fold, 4.14-fold, 3.14-fold, and 2.53-fold at −75° C., −20° C., 20° C., 40° C., and 60° C., respectively, as compared to the absence of ATT (see Table 3 above).

In summary, these data demonstrated that ATT stabilized coelenterazine against decomposition over time at different temperatures, and thus, inclusion of ATT in a solution, in which coelenterazine may be incubated or stored for a period of time, may suppress or reduce the decomposition of coelenterazine (i.e., stabilize coelenterazine).

Example 2

Stability of Coelenterazine-h

The stability of coelenterazine-h in the presence and absence of ATT was measured over time at different temperatures. Specifically, 1.25 mM coelenterazine-h was present in a solution of 50% ethanol and 50% propylene glycol (i.e., the solution without ATT) or a solution of 50% ethanol and 50% propylene glycol with 225 mM ATT (i.e., the solution with ATT). These two solutions were incubated at −20° C., room temperature (RT), 40° C., or 60° C. and analyzed at for 0 days, 1 day, 3 days, 7 days, 15 days, and 30 days.

Following incubation, high performance liquid chromatography (HPLC) was utilized to identify the components of the respective solutions at each time point. Specifically, an Agilent 1100 HPLC instrument was used and equipped with a quaternary pump, thermostatted autosampler and column compartment, and a G1311B diode-array detector. The column used was a Synergi-MAX-RP (Phenomenex, Torrance, Calif.) 100 AÅ 50×4.6 2.5 µm. The run on the HPLC was a gradient run with 0.1% TFA in water and acetonitrile. Absorbance was measured at 262 nanometers (nm). Standards of coelenterazine-h and its known degradants were run to confirm both the retention time and absorbance trace. 5 µl of each solution was injected and the retention time of coelenterazine-h was 4.7 minutes at room temperature.

Figure 2A:
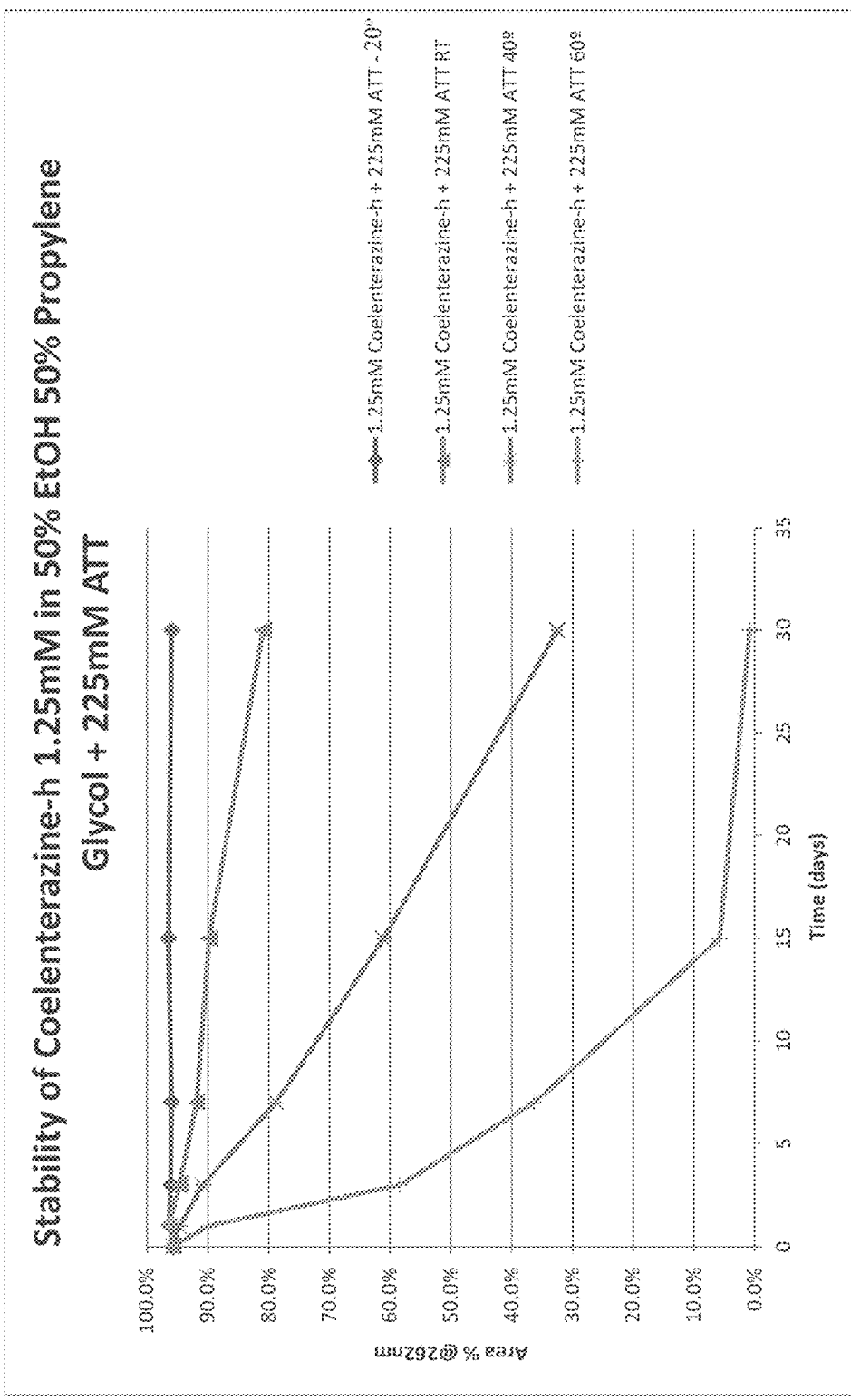
FIG. 2A shows the stability of coelenterazine-h in the presence of ATT.
Figure 2B:
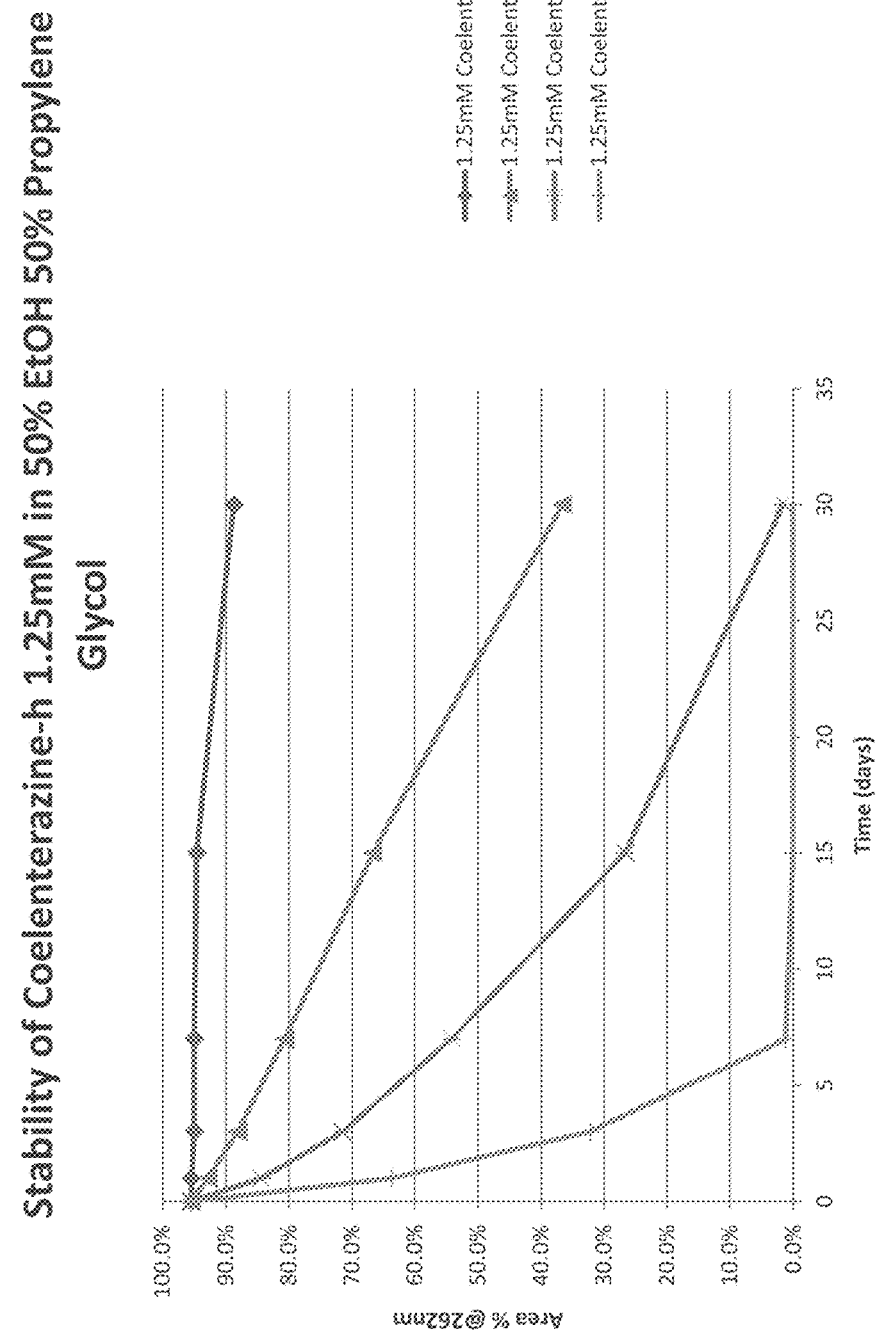
FIG. 2B shows the stability of coelenterazine-h in the absence of ATT.

The results of the HPLC analysis are shown below in Tables 4 and 5 and FIGS. 2A and 2B, in which the values are reported as relative peak area percentage at 262 nm (i.e., the lamba max of the substrate). FIG. 2A shows the relative peak area percentage of the solution with ATT over time (in days) while FIG. 2B shows the relative peak area percentage of the solution without ATT over time (in days). In each of FIGS. 2A and 2B, diamond is 1.25 mM coelenterazine-h incubated over time with or without 225 mM ATT, respectively, at −20° C., triangle is 1.25 mM coelenterazine-h incubated over time with or without 225 mM ATT, respectively, at room temperature (RT), star is 1.25 mM coelenterazine-h incubated over time with or without 225 mM ATT, respectively, at 40° C., and cross is 1.25 mM coelenterazine-h incubated over time with or without 225 mM ATT, respectively, at 60° C.

TABLE 4

| | Temperature (in Celsius) | | | |
| --- | --- | --- | --- | --- |
| | −20° | | RT | |
| Time (days) | 1.25 mM Coelenterazine-h (15-957-39) with 225 mM ATT | 1.25 mM Coelenterazine-h (15-957-39) | 1.25 mM Coelenterazine-h (15-957-39) with 225 mM ATT | 1.25 mM Coelenterazine-h (15-957-39) |
| 0 | 95.7% | 95.5% | 95.7% | 95.5% |
| 1 | 96.3% | 95.4% | 96.4% | 92.9% |
| 3 | 96.1% | 95.0% | 94.6% | 88.1% |
| 7 | 95.9% | 95.0% | 91.8% | 80.7% |
| 15 | 96.4% | 94.6% | 89.8% | 66.7% |
| 30 | 95.9% | 88.8% | 80.9% | 36.6% |

TABLE 5

| | Temperature (in Celsius) | | | |
| --- | --- | --- | --- | --- |
| | 40° | | 60° | |
| Time (days) | 1.25 mM Coelenterazine-h (15-957-39) with 225 mM ATT | 1.25 mM Coelenterazine-h (15-957-39) | 1.25 mM Coelenterazine-h (15-957-39) with 225 mM ATT | 1.25 mM Coelenterazine-h (15-957-39) |
| 0 | 95.7% | 95.5% | 95.7% | 95.5% |
| 1 | 94.7% | 84.3% | 90.0% | 63.6% |
| 3 | 90.8% | 71.5% | 58.3% | 32.3% |
| 7 | 78.8% | 54.2% | 36.3% | 1.2% |
| 15 | 61.0% | 26.7% | 5.8% | ND* |
| 30 | 32.5% | 1.6% | 0.9% | ND* |

*ND = not determined.

From the HPLC analysis, the half-life of coelenterazine-h in the presence of ATT at 40° C. and 60° C. was calculated to be 20 days and 5 days, respectively, while the half-life of coelenterazine-h in the absence of ATT at 20° C., 40° C. and 60° C. was calculated to be 24 days, 7.5 days and 2 days, respectively (see Table 6 below).

TABLE 6

| Temperature | Estimated from graph | | Calculated from Arrhenius | | |
|---|---|---|---|---|---|
| | $T_{1/2}$ coel-h + ATT | $T_{1/2}$ coel-h no ATT | $T_{1/2}$ coel-h + ATT | $T_{1/2}$ coel-h no ATT | Fold Stabilizing |
| −75° C. | | | 2.00E+05 years | 1.00E+04 years | 20.00 |
| −20° C. | | | 9480 years | 3.3 years | 2872.73 |
| 20° C. | | 24 days | 118 days | 23.2 days | 5.09 |
| 40° C. | 20 days | 7.5 days | 20 days | 4.7 days | 4.26 |
| 60° C. | 5 days | 2 days | 4.2 days | 1.2 days | 3.50 |

Additionally, Arrhenius plots were generated for coelenterazine-h in the presence and absence of ATT to calculate the half-life of coelenterazine-h at various temperatures. The Arrhenius equation is as follows:

$$k = Ae^{\frac{-E_a}{RT}}.$$

The transformed equation is as follows:

$$\ln(k) = \ln(A) - \frac{E_a}{R} \cdot \frac{1}{T}.$$

Figure 9:
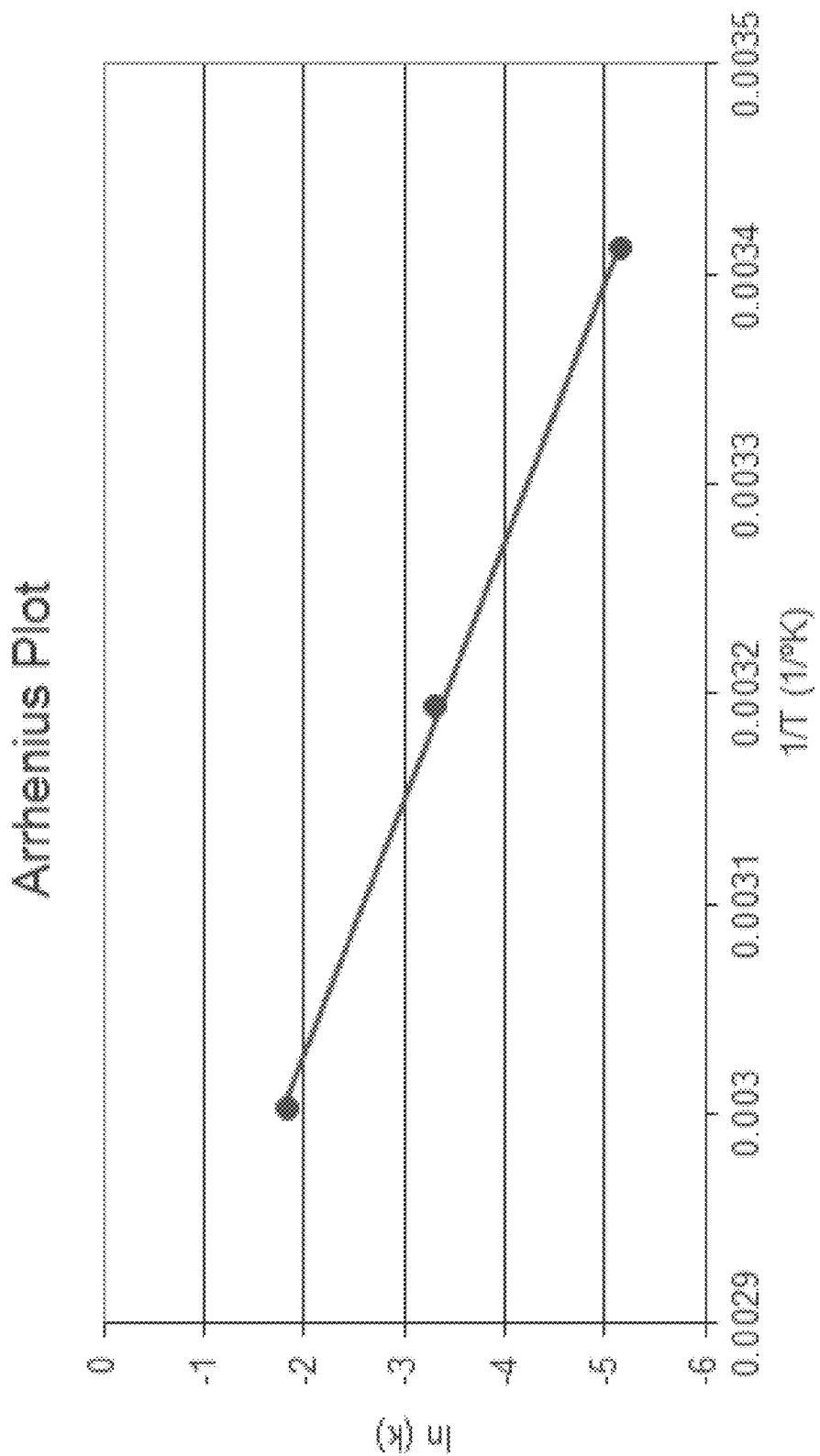
FIG. 9 shows an Arrhenius plot for coelenterazine-h in the presence of ATT.

The Arrhenius plot for coelenterazine-h in the presence of ATT is shown in FIG. 9. In FIG. 9, the slope was −8131.2, the intercept was 22.6157, and $R^2$ was 0.9994.

Figure 10:
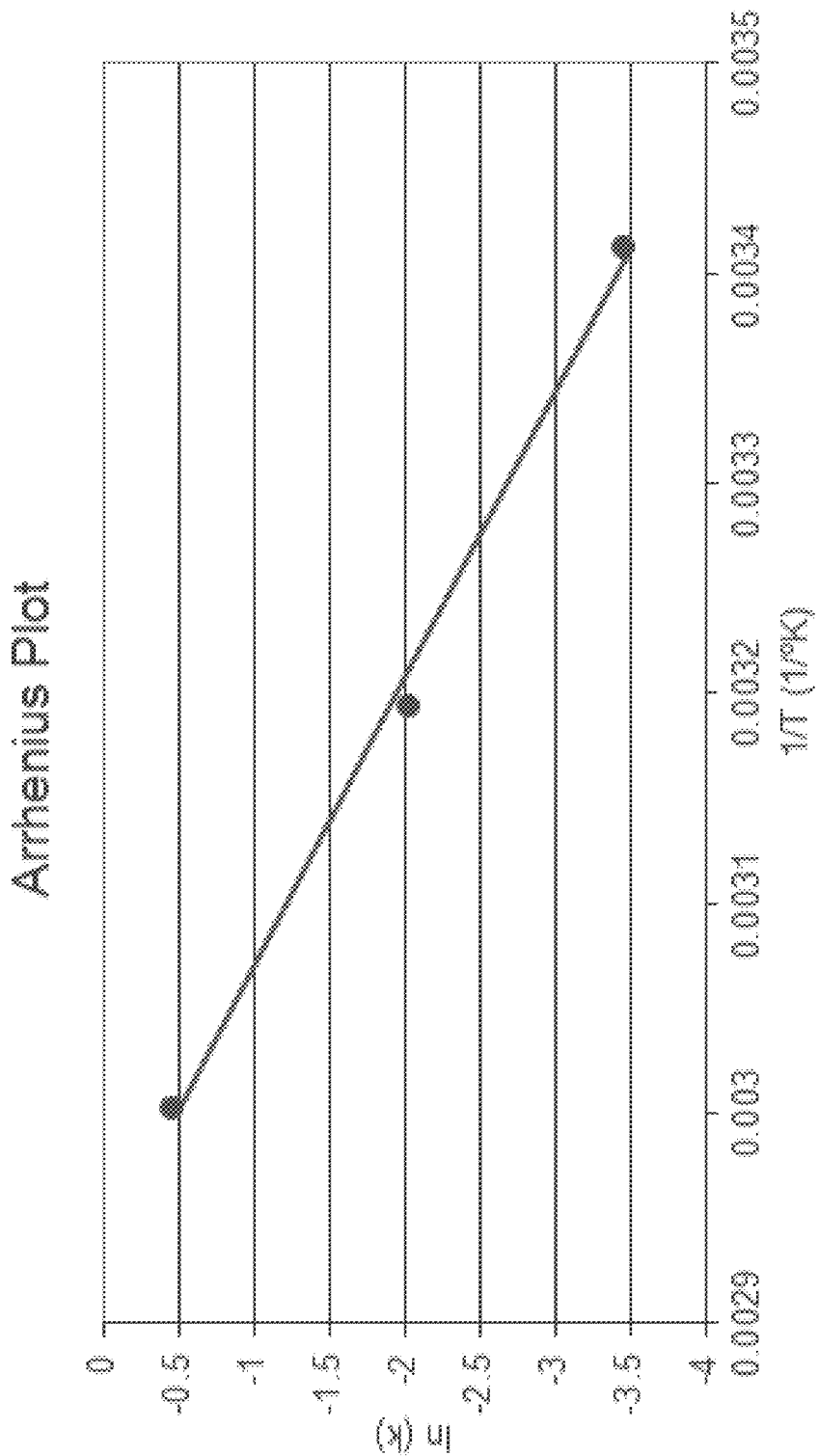
FIG. 10 shows an Arrhenius plot for coelenterazine-h in the absence of ATT.

The Arrhenius plot for coelenterazine-h in the absence of ATT is shown in FIG. 10. In FIG. 10, the slope was −7310.53, the intercept was 21.4386, and $R^2$ was 0.9964.

Additionally, the calculated half-lives from the Arrhenius plot indicated that the presence of ATT stabilized coelenterazine against decomposition 20.00-fold, 2872.73-fold, 5.09-fold, 4.26-fold, and 3.50-fold at −75° C., −20° C., 20° C., 40° C., and 60° C., respectively, as compared to the absence of ATT (see Table 6 above).

In summary, these data demonstrated that ATT stabilized coelenterazine-h against decomposition over time at different temperatures, and thus, inclusion of ATT in a solution, in which coelenterazine-h may be incubated or stored for a period of time, may suppress or reduce the decomposition of coelenterazine-h (i.e., stabilize coelenterazine-h).

Example 3

Stability of Coelenterazine-h-h

The stability of coelenterazine-h-h in the presence and absence of ATT was measured over time at different temperatures. Specifically, 1.25 mM coelenterazine-h-h was present in a solution of 50% ethanol and 50% propylene glycol (i.e., the solution without ATT) or a solution of 50% ethanol and 50% propylene glycol with 225 mM ATT (i.e., the solution with ATT). These two solutions were incubated at −20° C., room temperature (RT), 40° C., or 60° C. and analyzed at 0 days, 1 day, 3 days, 7 days, 15 days, and 30 days.

Following incubation, high performance liquid chromatography (HPLC) was utilized to identify the components of the respective solutions at each time point. Specifically, an Agilent 1100 HPLC instrument was used and equipped with a quaternary pump, thermostatted autosampler and column compartment, and a G1311B diode-array detector. The column used was a Synergi-MAX-RP (Phenomenex, Torrance, Calif.) 100 AÅ 50×4.6 2.5 μm. The run on the HPLC was a gradient run with 0.1% TFA in water and acetonitrile. Absorbance was measured at 262 nanometers (nm). Standards of coelenterazine-h-h and its known degradants were run to confirm both the retention time and absorbance trace. 5 μl of each solution was injected and the retention time of coelenterazine-h-h at room temperature was 5.5 minutes.

Figure 3A:
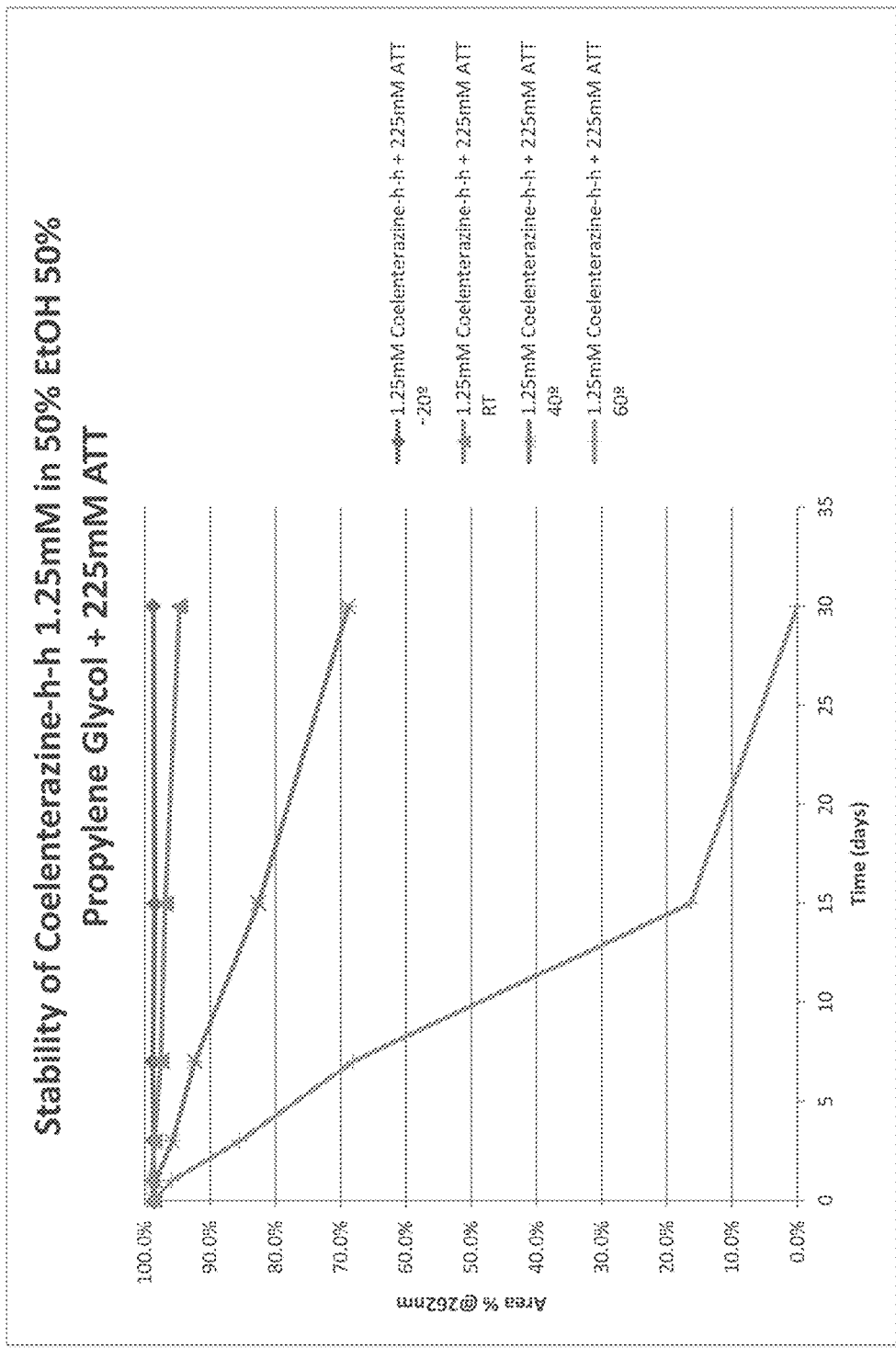
FIG. 3A shows the stability of coelenterazine-h-h in the presence of ATT.
Figure 3B:
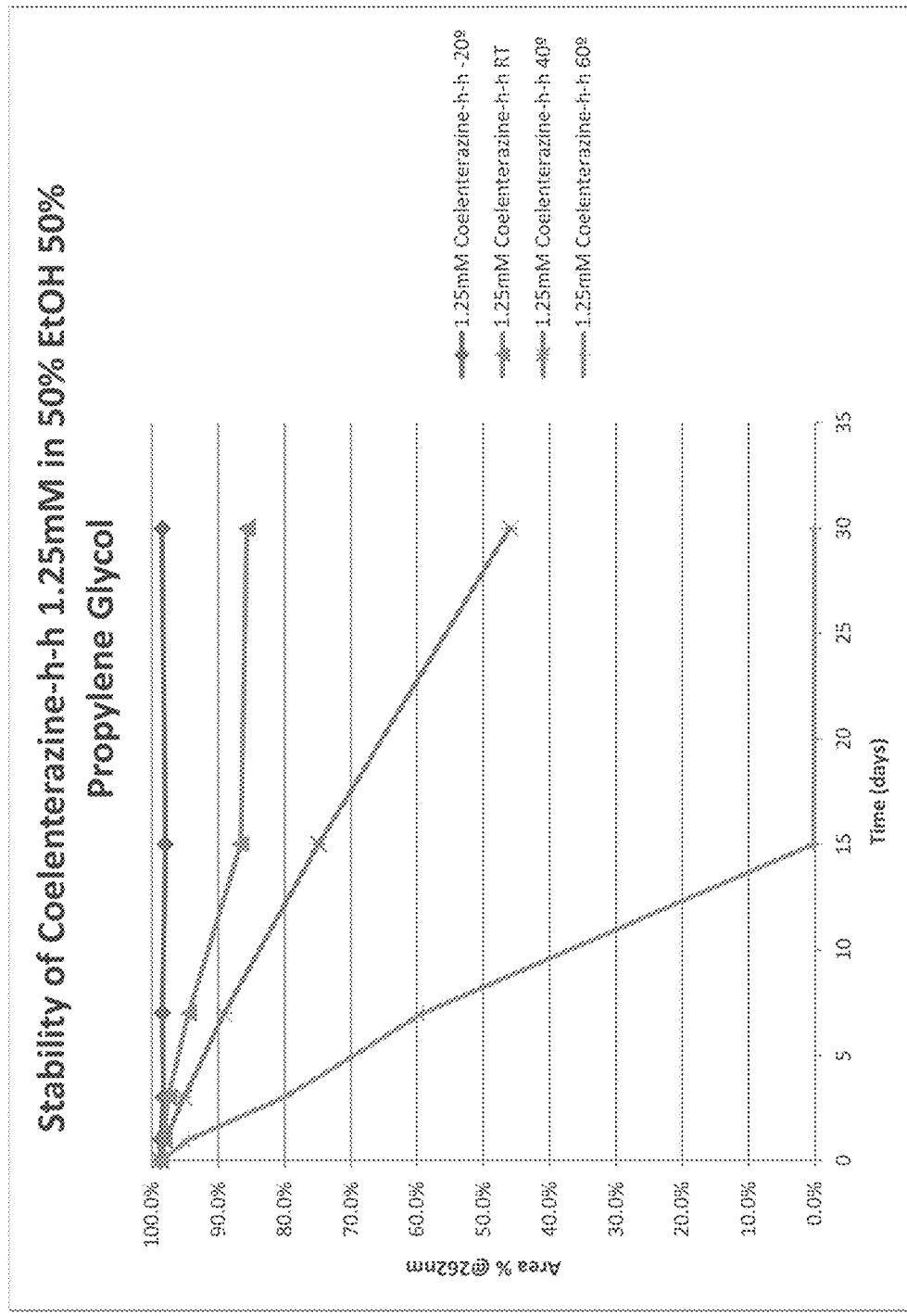
FIG. 3B shows the stability of coelenterazine-h-h in the absence of ATT.

The results of the HPLC analysis are shown below in Tables 7 and 8 and FIGS. 3A and 3B, in which the values are reported as relative peak area percentage at 262 nm (i.e., the lamba max of the substrate). FIG. 3A shows the relative peak area percentage of the solution with ATT over time (in days) while FIG. 3B shows the relative peak area percentage of the solution without ATT over time (in days). In each of FIGS. 3A and 3B, diamond is 1.25 mM coelenterazine-h-h incubated over time with or without 225 mM ATT, respectively, at −20° C., triangle is 1.25 mM coelenterazine-h-h incubated over time with or without 225 mM ATT, respectively, at room temperature (RT), star is 1.25 mM coelenterazine-h-h incubated over time with or without 225 mM ATT, respectively, at 40° C., and cross is 1.25 mM coelenterazine-h-h incubated over time with or without 225 mM ATT, respectively, at 60° C.

TABLE 7

| | Temperature (in Celsius) | | | |
|---|---|---|---|---|
| | −20° | | RT | |
| Time (days) | 1.25 mM Coelenterazine-h-h (1193-25-1) with 225 mM ATT | 1.25 mM Coelenterazine-h-h (1193-25-1) | 1.25 mM Coelenterazine-h-h (1193-25-1) with 225 mM ATT | 1.25 mM Coelenterazine-h-h (1193-25-1) |
| 0 | 98.6% | 98.7% | 98.6% | 98.7% |
| 1 | 98.6% | 98.6% | 99.0% | 98.2% |
| 3 | 98.7% | 98.2% | 98.5% | 97.5% |
| 7 | 98.8% | 98.4% | 97.5% | 94.4% |
| 15 | 98.5% | 97.9% | 96.9% | 86.6% |
| 30 | 98.7% | 98.5% | 94.7% | 85.7% |

TABLE 8

| | Temperature (in Celsius) | | | |
|---|---|---|---|---|
| | 40° | | 60° | |
| Time (days) | 1.25 mM Coelenterazine-h-h (1193-25-1) with 225 mM ATT | 1.25 mM Coelenterazine-h-h (1193-25-1) | 1.25 mM Coelenterazine-h-h (1193-25-1) with 225 mM ATT | 1.25 mM Coelenterazine-h-h (1193-25-1) |
| 0 | 98.6% | 98.7% | 98.6% | 98.7% |
| 1 | 98.3% | 98.0% | 95.9% | 94.3% |

TABLE 8-continued

| | Temperature (in Celsius) | | | |
|---|---|---|---|---|
| | 40° | | 60° | |
| Time (days) | 1.25 mM Coelenterazine-h-h (1193-25-1) with 225 mM ATT | 1.25 mM Coelenterazine-h-h (1193-25-1) | 1.25 mM Coelenterazine-h-h (1193-25-1) with 225 mM ATT | 1.25 mM Coelenterazine-h-h (1193-25-1) |
| 3 | 95.8% | 95.1% | 85.5% | 80.0% |
| 7 | 92.3% | 89.1% | 68.2% | 59.1% |
| 15 | 82.6% | 74.9% | 16.3% | 0.2% |
| 30 | 68.8% | 46.0% | ND* | ND |

*ND = not determined.

From the HPLC analysis, the half-life of coelenterazine-h-h in the presence of ATT at 60° C. was calculated to be 10 days while the half-life of coelenterazine-h-h in the absence of ATT at 40° C. and 60° C. was calculated to be 27 days and 8 days, respectively (see Table 9 below).

TABLE 9

| | Estimated from graph | | Calculated from Arrhenius | | |
|---|---|---|---|---|---|
| Temperature | $T_{1/2}$ coel-h-h + ATT | $T_{1/2}$ coel-h-h no ATT | $T_{1/2}$ coel-h-h + ATT | $T_{1/2}$ coel-h-h no ATT | Fold Stabilizing |
| −75° C. | | | 6.10E+07 years | 1.70E+07 years | 3.59 |
| −20° C. | | | 460 years | 147.5 years | 3.12 |
| 20° C. | | | 510 days | 172 days | 2.97 |
| 40° C. | | 27 days | 49 days | 16.9 days | 2.90 |
| 60° C. | 10 days | 8 days | 6.2 days | 2.2 days | 2.82 |

Additionally, Arrhenius plots were generated for coelenterazine-h-h in the presence and absence of ATT to calculate the half-life of coelenterazine-h-h at various temperatures. The Arrhenius equation is as follows:

$$k = Ae^{\frac{-E_a}{RT}}.$$

The transformed equation is as follows:

$$\ln(k) = \ln(A) - \frac{E_a}{R} \cdot \frac{1}{T}.$$

Figure 11:
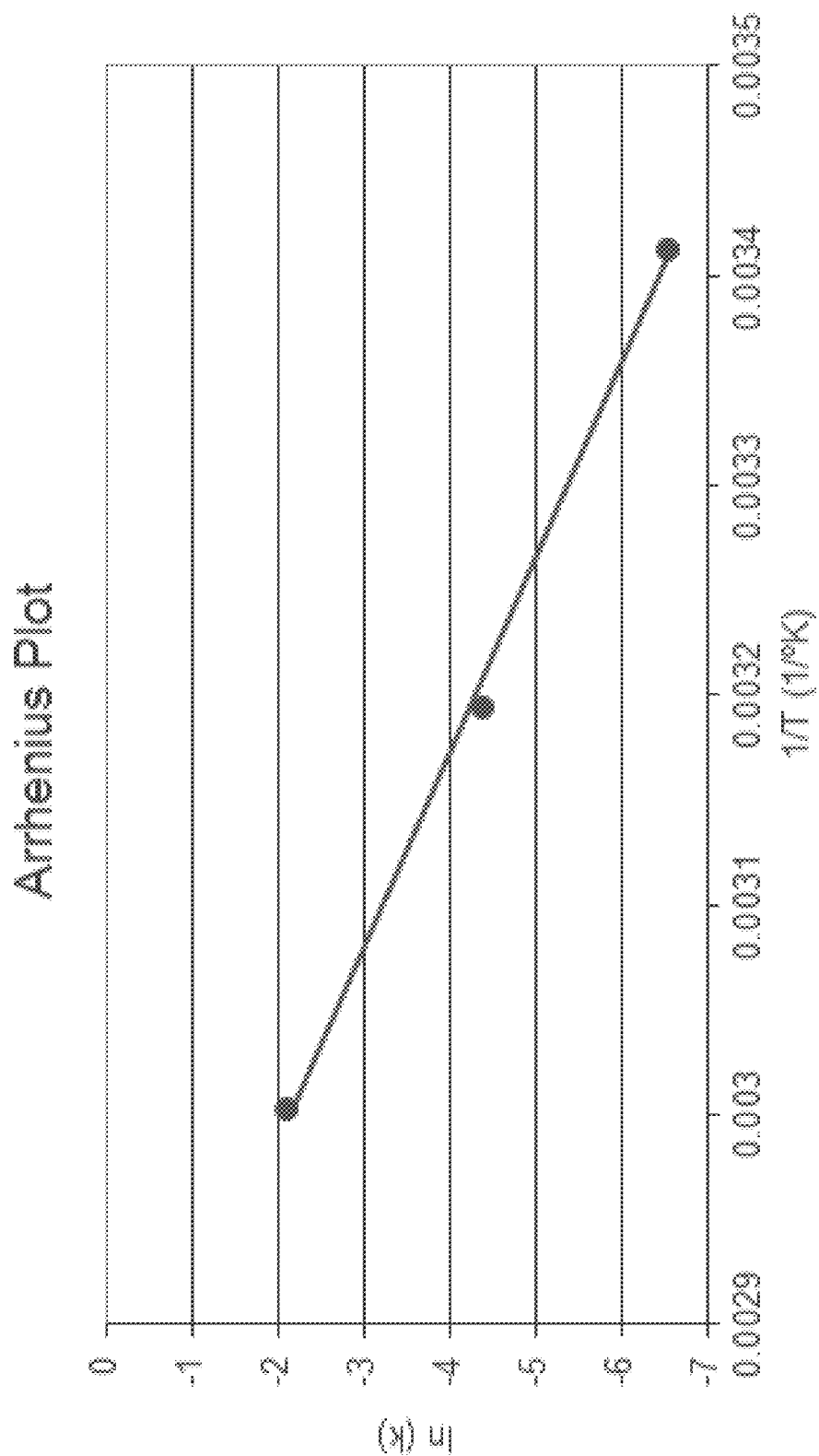
FIG. 11 shows an Arrhenius plot for coelenterazine-h-h in the presence of ATT.

The Arrhenius plot for coelenterazine-h-h in the presence of ATT is shown in FIG. 11. In FIG. 11, the slope was −10740.9, the intercept was 30.0575, and $R^2$ was 0.9967.

Figure 12:
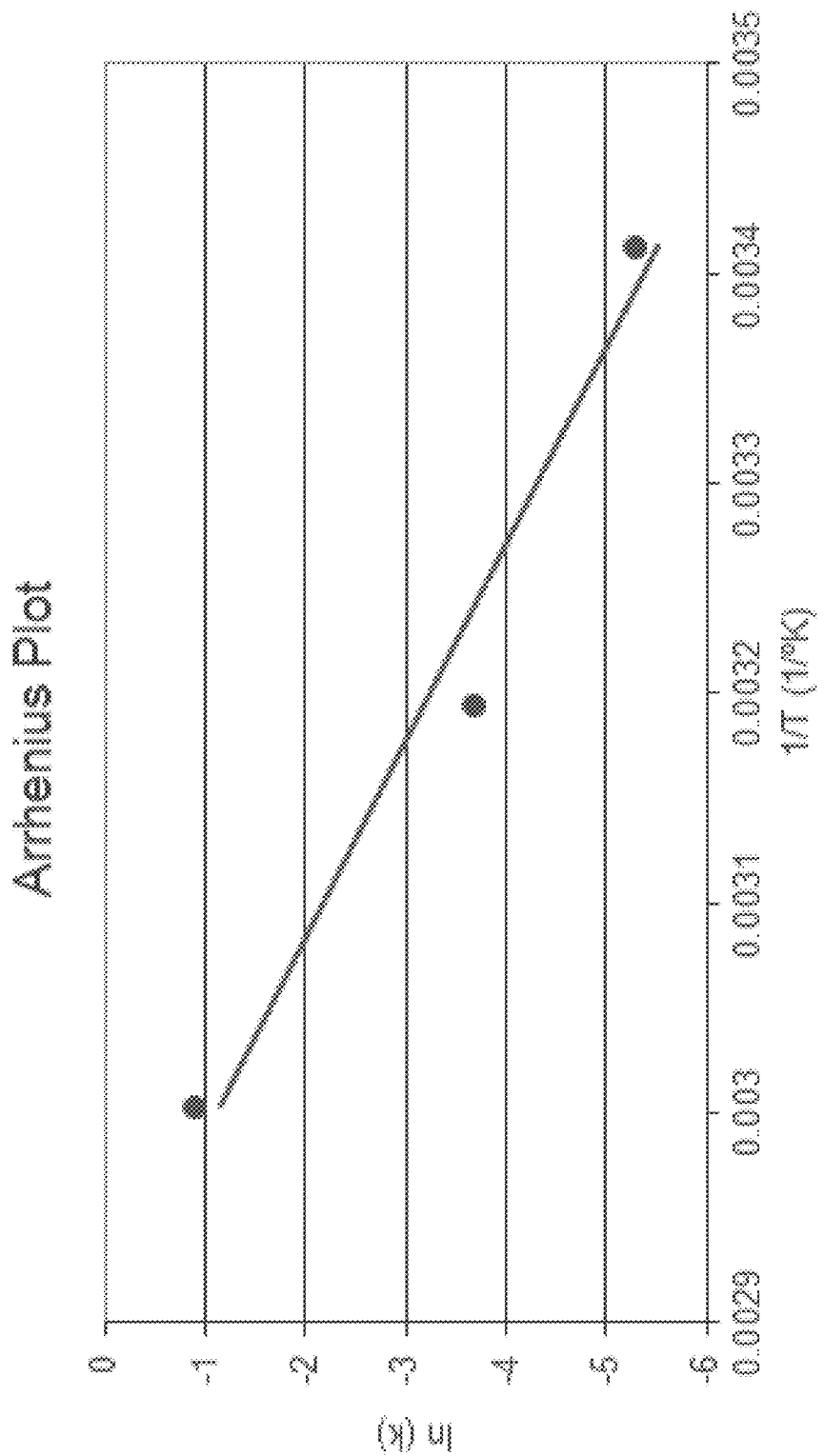
FIG. 12 shows an Arrhenius plot for coelenterazine-h-h in the absence of ATT.

The Arrhenius plot for coelenterazine-h-h in the absence of ATT is shown in FIG. 12. In FIG. 12, the slope was 30.8352, the intercept was −10650.1, and $R^2$ was 0.9648.

Additionally, the calculated half-lives from the Arrhenius plot indicated that the presence of ATT stabilized coelenterazine against decomposition 3.59-fold, 3.12-fold, 2.97-fold, 2.90-fold, and 2.82-fold at −75° C., −20° C., 20° C., 40° C., and 60° C., respectively, as compared to the absence of ATT (see Table 9 above).

In summary, these data demonstrated that ATT stabilized coelenterazine-h-h against decomposition over time at different temperatures, and thus, inclusion of ATT in a solution, in which coelenterazine-h-h may be incubated or stored for a period of time, may suppress or reduce the decomposition of coelenterazine-h-h (i.e., stabilize coelenterazine-h-h).

Example 4

Stability of Furimazine

The stability of furimazine in the presence and absence of ATT was measured over time at different temperatures. This study was conducted in the presence of light. Specifically, 1.25 mM furimazine was present in a solution of 50% ethanol and 50% propylene glycol (i.e., the solution without ATT) or a solution of 50% ethanol and 50% propylene glycol with 225 mM ATT (i.e., the solution with ATT). These two solutions were incubated at −20° C., room temperature (RT, i.e., 20° C.), 40° C., or 60° C. and analyzed at 0 days, 1 day, 3 days, 7 days, 15 days, 30 days and 90 days.

Following incubation, high performance liquid chromatography (HPLC) was utilized to identify the components of the respective solutions at each time point. Specifically, an Agilent 1100 HPLC instrument was used and equipped with a quaternary pump, thermostatted autosampler and column compartment, and a G1311B diode-array detector. The column used was a Synergi-MAX-RP (Phenomenex, Torrance, Calif.) 100 AÅ 50×4.6 2.5 μm. The run on the HPLC was a gradient run with 0.1% TFA in water and acetonitrile. Absorbance was measured at 262 nanometers (nm). Standards of furimazine and its known degradants were run to confirm both the retention time and absorbance trace. 5 μl of each solution was injected and the retention time of furimazine at room temperature was 5.1 minutes.

Figure 4A:
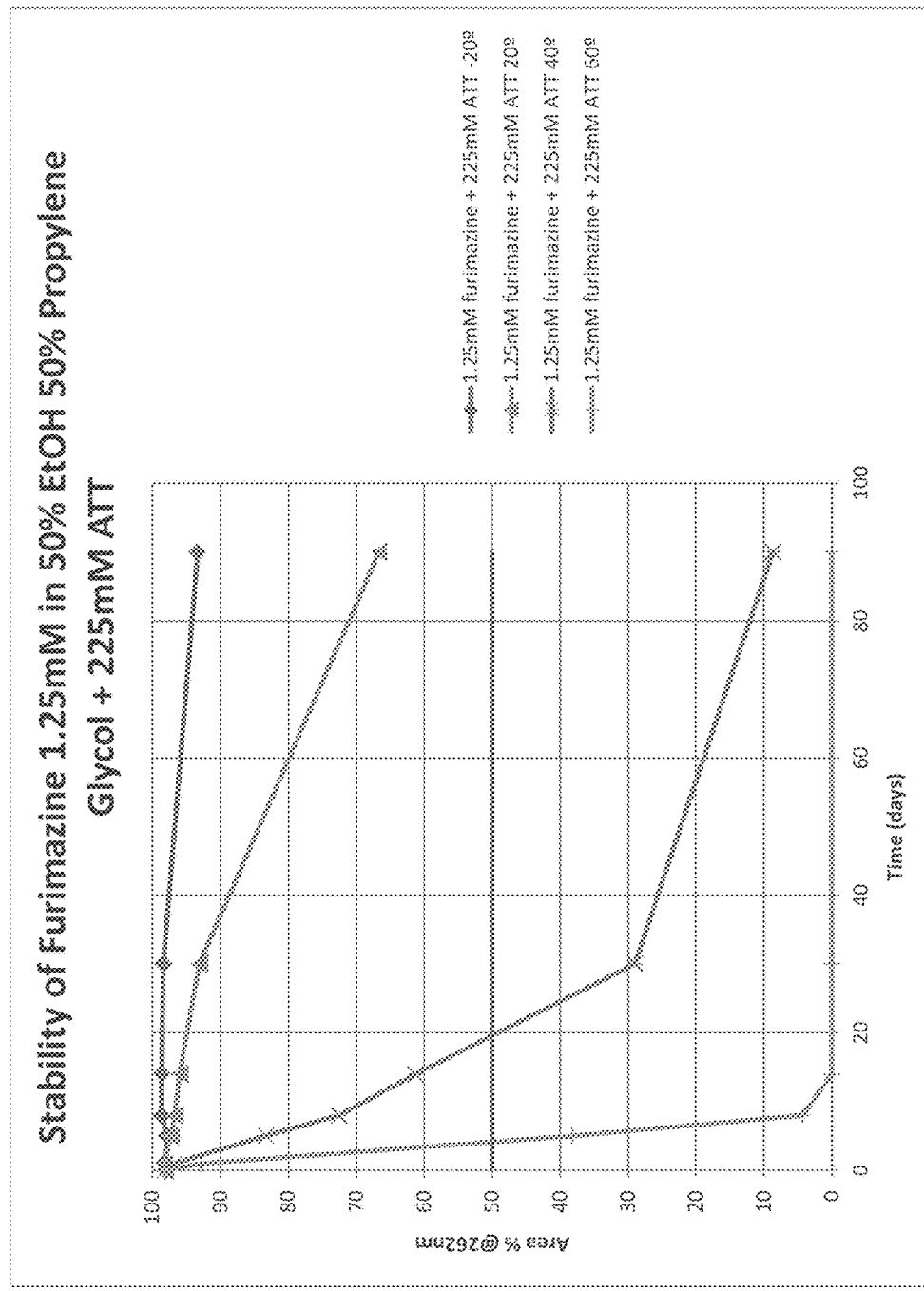
FIG. 4A shows the stability of furimazine in the presence of ATT.
Figure 4B:
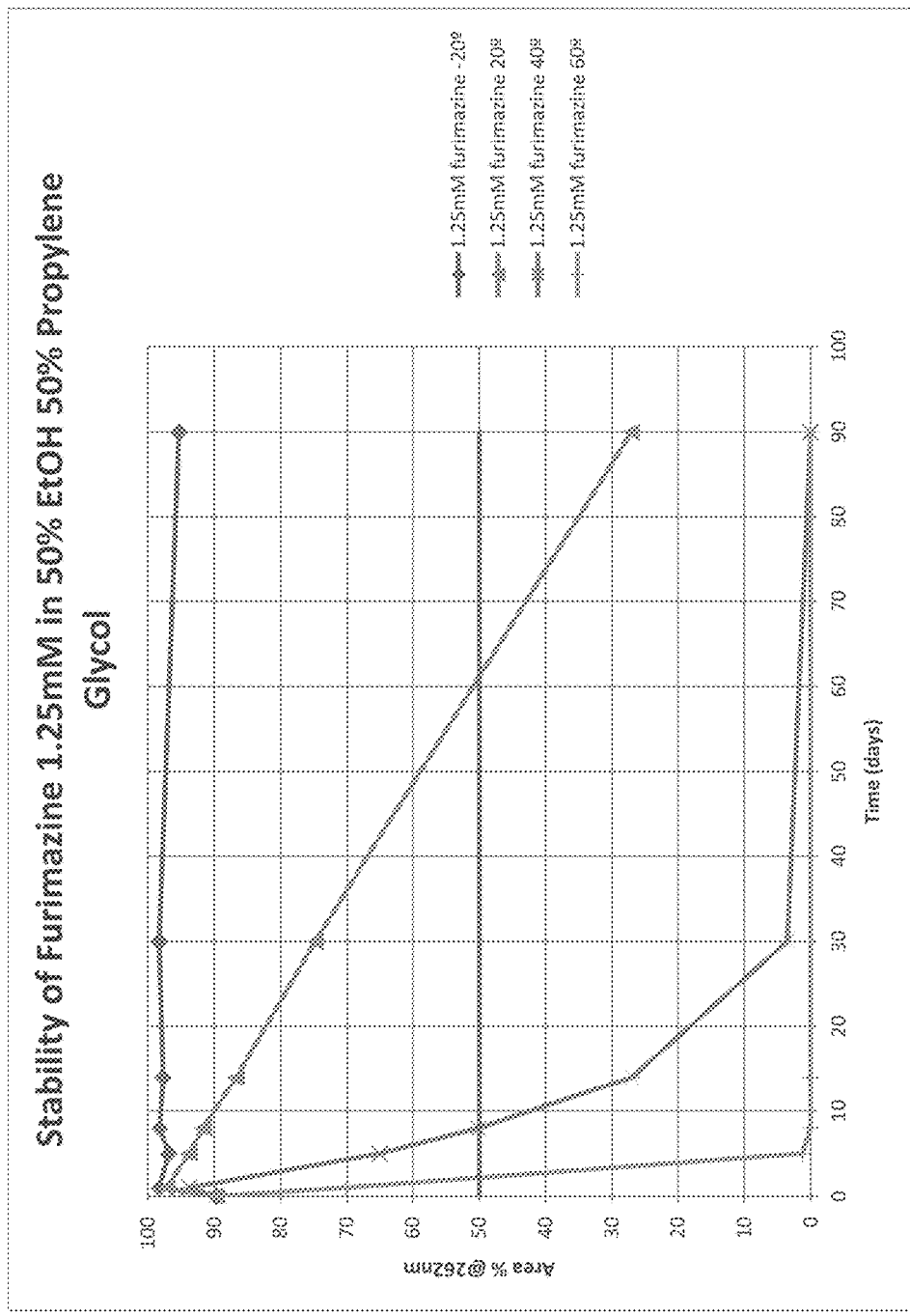
FIG. 4B shows the stability of furimazine in the absence of ATT.

The results of the HPLC analysis are shown below in Tables 10 and 11 and FIGS. 4A and 4B, in which the values are reported as relative peak area percentage at 262 nm (i.e., the lamba max of the substrate). FIG. 4A shows the relative peak area percentage of the solution with ATT over time (in days) while FIG. 4B shows the relative peak area percentage of the solution without ATT over time (in days). In each of FIGS. 4A and 4B, diamond is 1.25 mM furimazine incubated over time with or without 225 mM ATT, respectively, at −20° C., triangle is 1.25 mM furimazine incubated over time with or without 225 mM ATT, respectively, at 20° C., star is 1.25 mM furimazine incubated over time with or without 225 mM ATT, respectively, at 40° C., and cross is 1.25 mM furimazine incubated over time with or without 225 mM ATT, respectively, at 60° C.

TABLE 10

| | Temperature (in Celsius) | | | |
|---|---|---|---|---|
| | −20° | | RT | |
| Time (days) | 1.25 mM Furimazine with 225 mM ATT | 1.25 mM Furimazine | 1.25 mM Furimazine with 225 mM ATT | 1.25 mM Furimazine |
| 0 | 98.1% | 89.7% | 98.1% | 89.7% |
| 1 | 98.3% | 98.3% | 98.2% | 97.2% |
| 5 | 97.9% | 96.9% | 97.3% | 93.8% |
| 8 | 98.6% | 98.2% | 96.7% | 91.7% |
| 14 | 98.6% | 97.7% | 96% | 86.7% |
| 30 | 98.4% | 98.3% | 93.1% | 74.8% |
| 90 | 93.34% | 95.3% | 66.7% | 27.1% |

TABLE 11

| | Temperature (in Celsius) | | | |
|---|---|---|---|---|
| | 40° | | 60° | |
| Time (days) | 1.25 mM Furimazine with 225 mM ATT | 1.25 mM Furimazine | 1.25 mM Furimazine with 225 mM ATT | 1.25 mM Furimazine |
| 0 | 98.1% | 89.7% | 98.1% | 89.7% |
| 1 | 96.9% | 93.8% | 92.9% | 70.1% |
| 5 | 83.4% | 65% | 38.2% | 1.3% |
| 8 | 72.6% | 50.1% | 4.3% | 0% |
| 14 | 61.2% | 27% | 0% | 0% |
| 30 | 29% | 3.5% | 0% | 0% |
| 90 | 8.66% | 0% | 0% | 0% |

From the HPLC analysis, the half-life of furimazine in the presence of ATT at 20° C., 40° C., and 60° C. was calculated to be 110 days, 20 days, and 5 days, respectively, while the half-life of furimazine in the absence of ATT at 20° C., 40° C., and 60° C. was calculated to be 61 days, 8 days, and 2.5 days, respectively (see Table 12 below).

TABLE 12

| | Estimated from graph | | Calculated from Arrhenius | | |
|---|---|---|---|---|---|
| Temperature | $T_{1/2}$ Fz + ATT | $T_{1/2}$ Fz no ATT | $T_{1/2}$ Fz + ATT | $T_{1/2}$ Fz no ATT | Fold Stabilizing |
| −75° C. | | | 2.60E+07 years | 2.20E+06 years | 11.82 |
| −20° C. | | | 179 years | 33 years | 5.42 |
| 20° C. | 110 days | 61 days | 189 days | 51.7 days | 3.66 |
| 40° C. | 20 days | 8 days | 17.9 days | 5.7 days | 3.14 |
| 60° C. | 5 days | 2.5 days | 2 days | 0.82 days | 2.44 |

Additionally, Arrhenius plots were generated for furimazine in the presence and absence of ATT to calculate the half-life of furimazine at various temperatures. The Arrhenius equation is as follows:

$$k = Ae^{\frac{-E_a}{RT}}.$$

The transformed equation is as follows:

$$\ln(k) = \ln(A) - \frac{E_a}{R} \cdot \frac{1}{T}.$$

Figure 5:
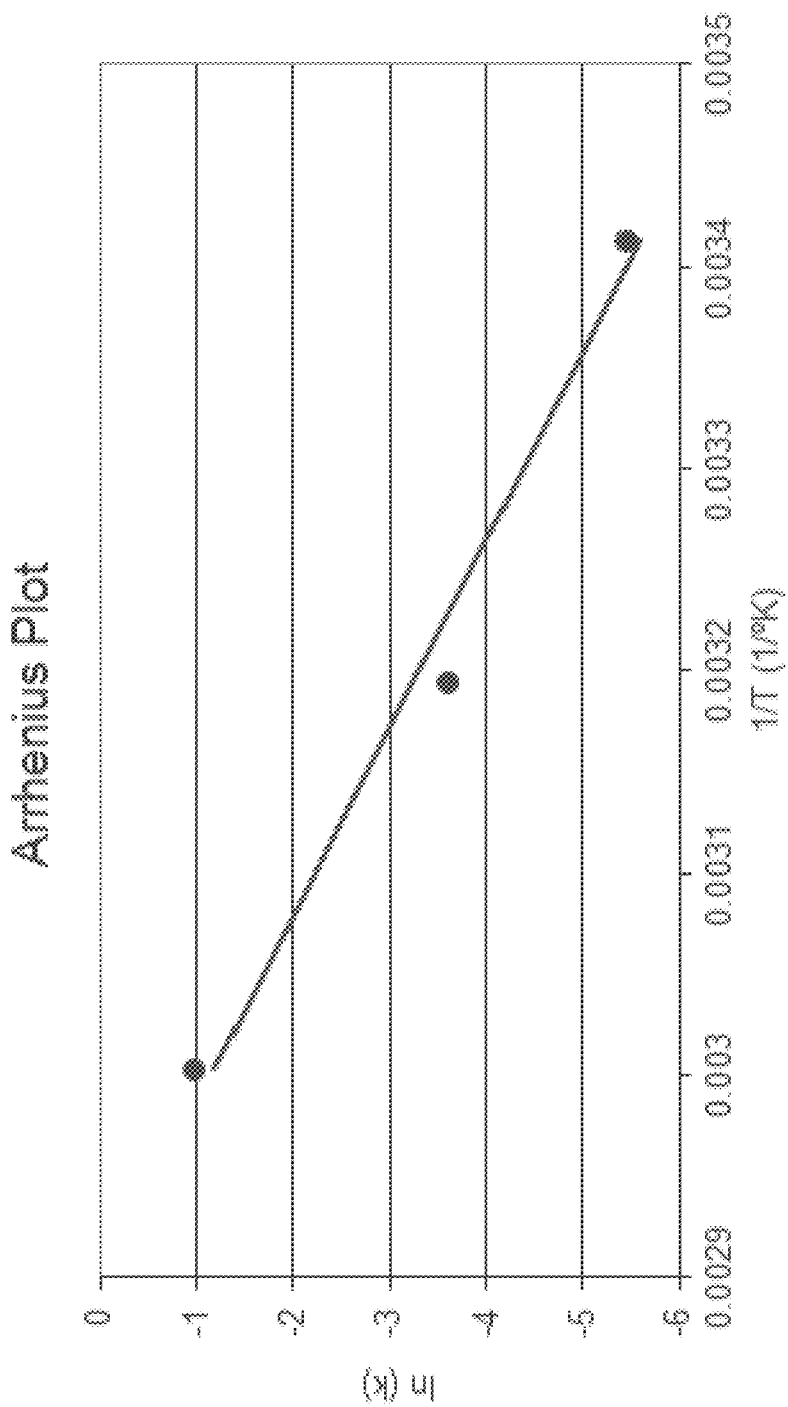
FIG. 5 shows an Arrhenius plot for furimazine in the presence of ATT.

The Arrhenius plot for furimazine in the presence of ATT is shown in FIG. 5. In FIG. 5, the slope was −10831.4, the intercept was 31.3561, and $R^2$ was 0.9813.

Figure 6:
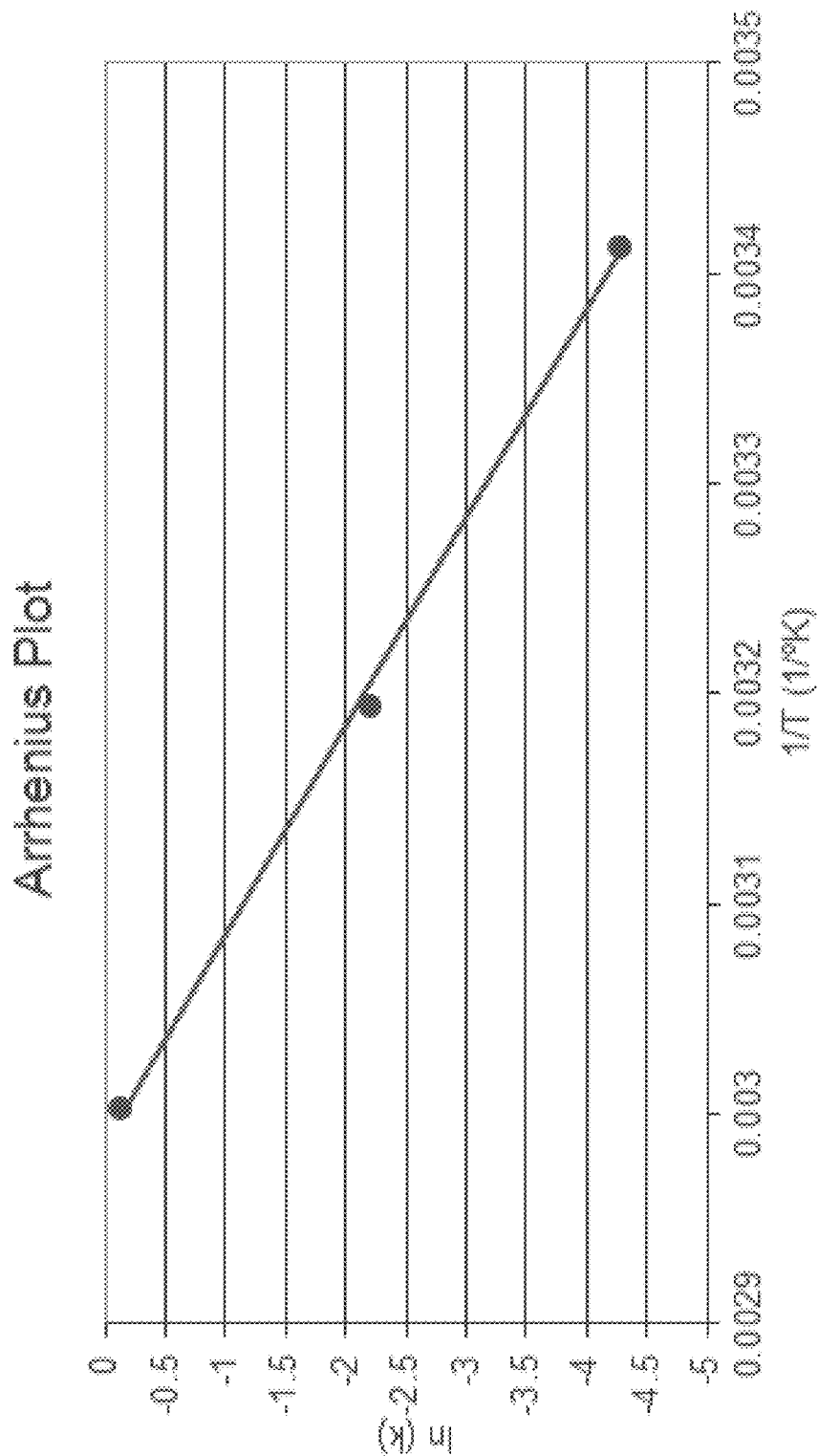
FIG. 6 shows an Arrhenius plot for furimazine in the absence of ATT.

The Arrhenius plot for furimazine in the absence of ATT is shown in FIG. 6. In FIG. 6, the slope was −10106.2, the intercept was 30.1809, and $R^2$ was 0.9984.

Additionally, the calculated half-lives from the Arrhenius plot indicated that the presence of ATT stabilized coelenterazine against decomposition 11.82-fold, 5.42-fold, 3.66-fold, 3.14-fold, and 2.44-fold at −75° C., −20° C., 20° C., 40° C., and 60° C., respectively, as compared to the absence of ATT (see Table 12 above).

In summary, these data demonstrated that ATT stabilized furimazine against decomposition over time at different temperatures, and thus, inclusion of ATT in a solution, in which furimazine may be incubated or stored for a period of time, may suppress or reduce the decomposition of furimazine (i.e., stabilize furimazine).

Example 5

Photostability of Furimazine

As described above, ATT stabilized furimazine against decomposition over time at different temperatures. Accordingly, furimazine was more thermostable in the presence of ATT than in the absence of ATT. Here, the photostability of furimazine in the presence and absence of ATT was examined at room temperature and 40° C.

Specifically, a 2× stock solution of ATT in 50% propylene glycol:50% ethanol (v/v) was prepared, in which the final concentration of ATT was 64.4 mg/mL. A 2× stock solution of furimazine in 50% propylene glycol:50% ethanol (v/v) was also prepared, in which the final concentration of furimazine was 0.95 mg/mL. In one vial, the 2×ATT stock solution was diluted 1:1 in the 2×furimazine stock solution to create a solution containing 225 mM ATT and 1.25 mM furimazine. In a second vial, the 2×furimazine stock solution was diluted 1:1 in 50% propylene glycol:50% ethanol (v/v) to create a control solution without the additive ATT (i.e., "no additive furimazine" control) and containing 1.25 mM furimazine.

The content of each vial was dispensed into separate, clear HPLC vials with insert and these HPLC vials were placed at room temperature (i.e., about 20° C.) in the light (i.e., in the presence of overhead fluorescent light) and at 40° C. in the light. There was one HPLC vial per time point for each temperature.

Figure 13A:
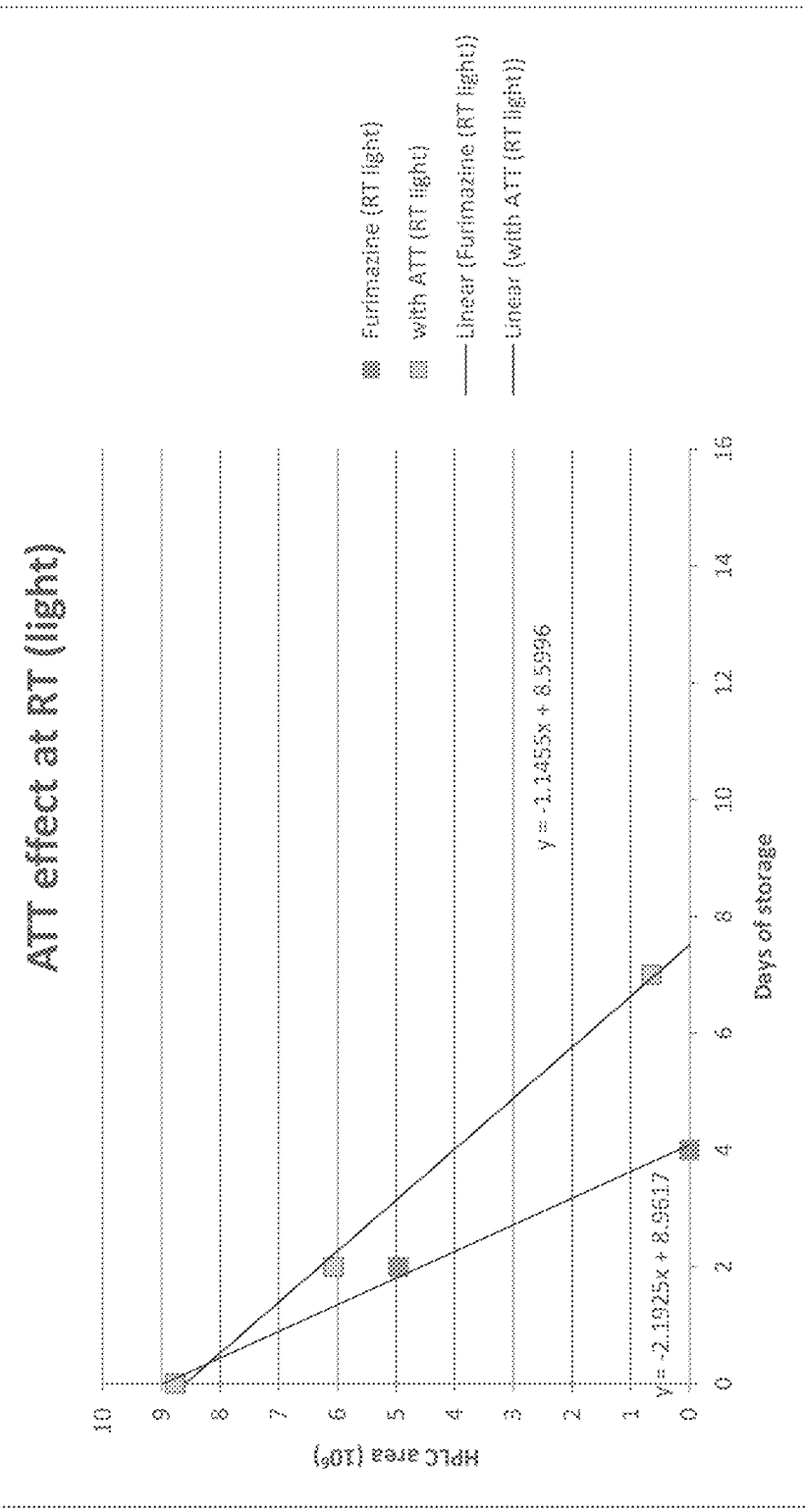
FIG. 13A shows the stability of furimazine in the presence of light and the presence or absence of ATT at room temperature.
Figure 13B:
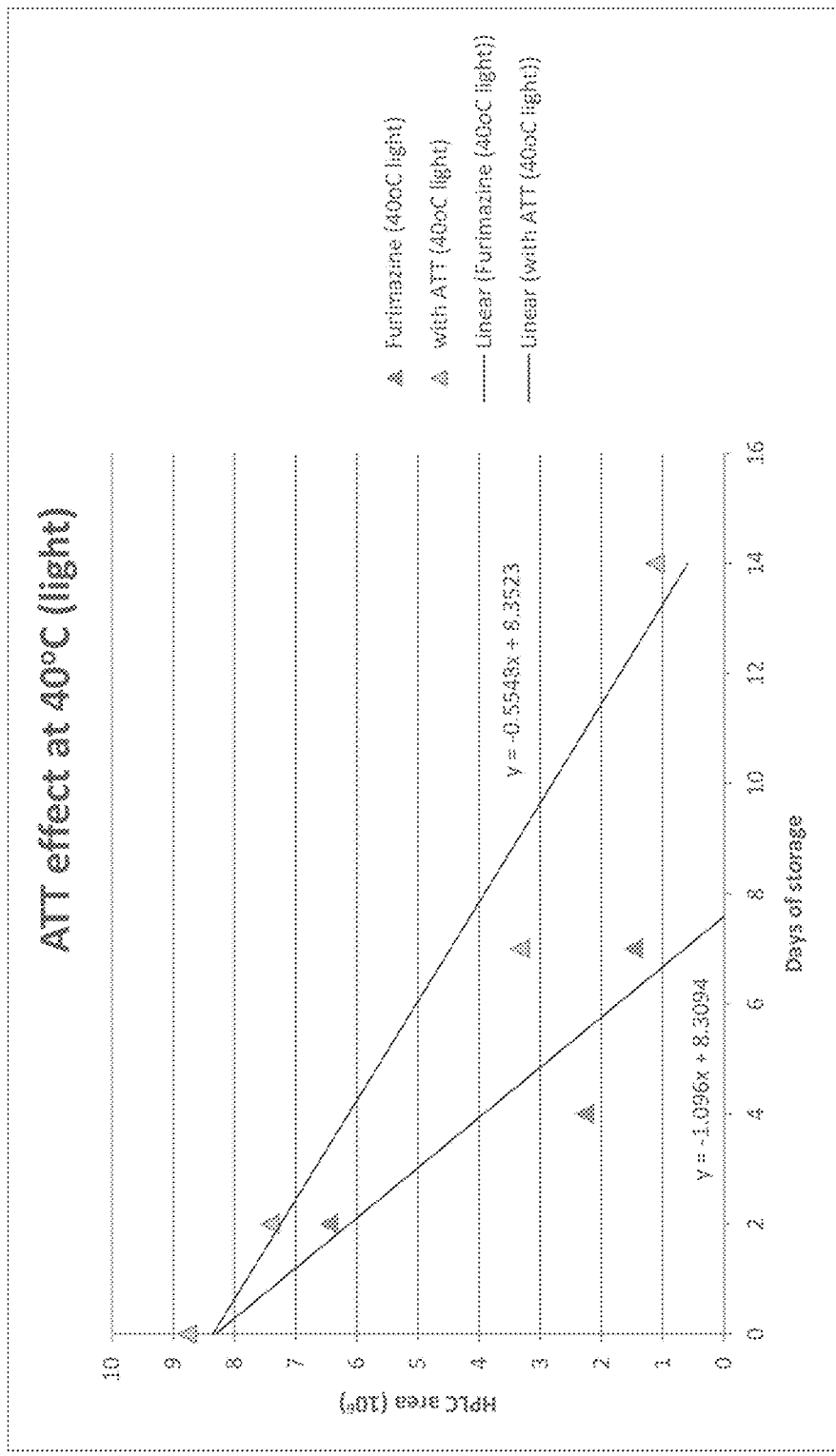
FIG. 13B shows the stability of furimazine in the presence of light and the presence or absence of ATT at 40° C.

Stability was measured by HPLC with 5 µL injection and detection at 262 nm. In each chromatogram, the area of the furimazine peak was determined. Stability curves were generated by plotting the area ($10^6$) vs. time (days) and are shown in FIGS. 13A and 13B for room temperature and 40° C., respectively. Stabilization was expressed as the fold increase in time it took furimazine to degrade 10% and 50% (i.e., half-life) in the presence of ATT (Tables 15 and 16). Table 3 shows the stability of furimazine in the light and in the presence and absence of ATT at room temperature. Table 4 shows the stability of furimazine in the light and in the presence and absence of ATT at 40° C.

TABLE 13

|  | Furimazine (no ATT) | Furimazine (with ATT) | Fold Increase in Stability |
|---|---|---|---|
| 10% loss (days) | 0.5 | 0.6 | 1.3 |
| 50% loss (days) | 2.1 | 3.7 | 1.8 |

TABLE 14

|  | Furimazine (no ATT) | Furimazine (with ATT) | Fold Increase in Stability |
|---|---|---|---|
| 10% loss (days) | 0.4 | 0.8 | 2.2 |
| 50% loss (days) | 3.6 | 7.2 | 2.0 |

Together, these data demonstrated that ATT stabilized furimazine against decomposition in the presence of light at different temperatures (e.g., room temperature and 40° C.), and thus, inclusion of ATT in a solution, in which furimazine may be incubated or stored for a period of time, may suppress or reduce decomposition of furimazine due to light exposure (i.e., photodegradation). Accordingly, ATT stabilized furimazine against photodegradation and thermal degradation.

Example 6

Stability of Furimazine

As described above, ATT stabilized furimazine against decomposition over time at different temperatures and in the presence of light. To further examine the stabilization of furimazine by ATT, stability of furimazine was measured at room temperature, 40°, and 60° C. in a different organic solvent, namely DMSO. This study was performed in the presence of light.

Specifically, a 2× stock solution of ATT in DMSO was prepared, in which the final concentration of ATT was 64.4 mg/mL. A 2× stock solution of furimazine in DMSO was also prepared, in which the final concentration of furimazine was 0.95 mg/mL. In one vial, the 2× ATT stock solution was diluted 1:1 in the 2× furimazine stock solution to create a solution containing 225 mM ATT and 1.25 mM furimazine. In a second vial, furimazine was diluted 1:1 in DMSO to create a control solution without the additive ATT (i.e., "no additive furimazine" control) and containing 1.25 mM furimazine.

The content of each vial was dispensed into separate, clear HPLC vials with insert and these HPLC vials were placed at room temperature (i.e., about 20° C.), 40° C., and 60° C. There was one HPLC vial per time point for each temperature.

Figure 14:
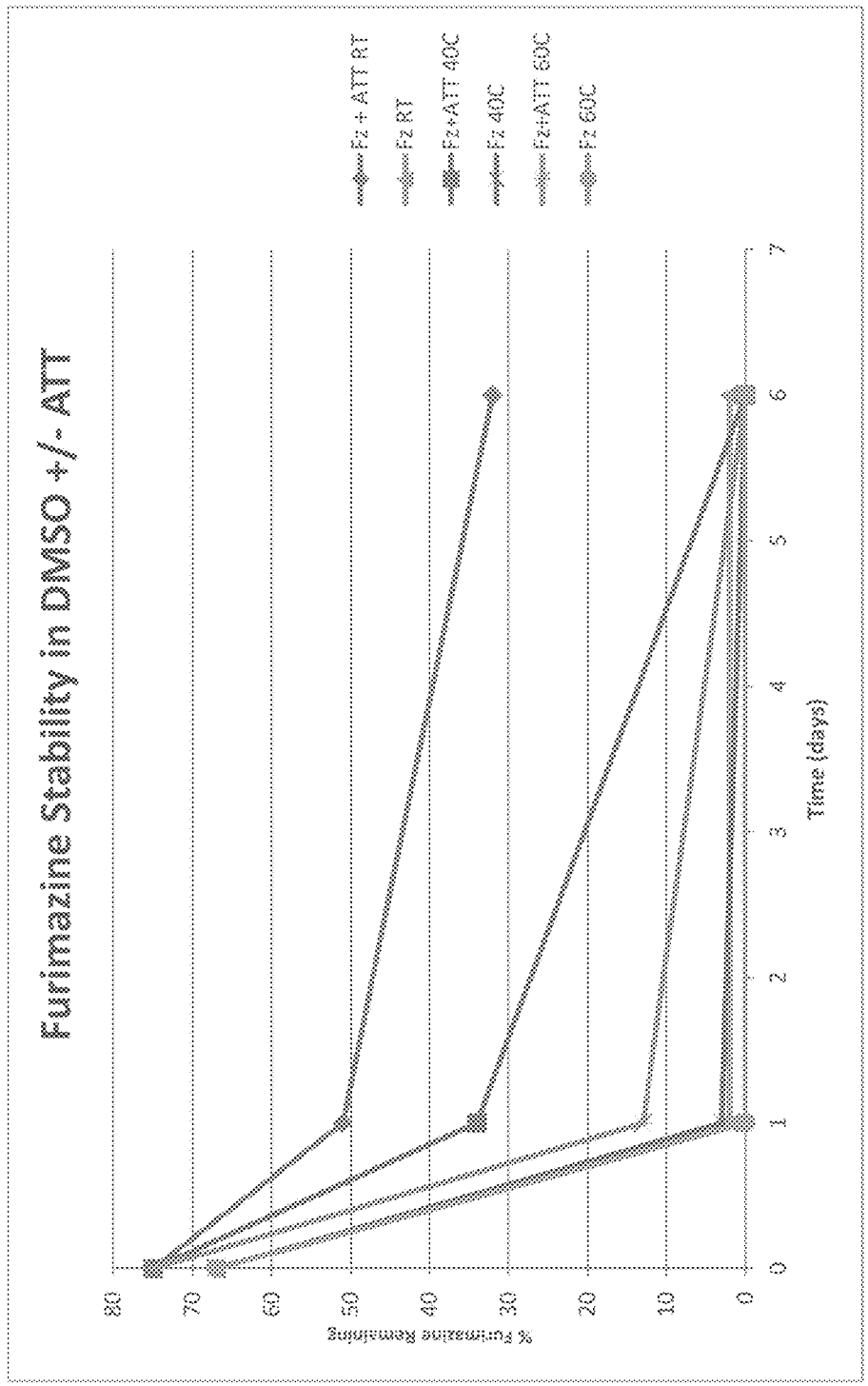
FIG. 14 shows the stability of furimazine in DMSO in the presence or absence of ATT at room temperature, 40° C., and 60° C.

Stability was measured by HPLC with 5 μL injection and detection at 262 nm. In each chromatogram, the area percentage of furimazine was determined. Stability curves were generated by plotting the area percentage vs. time (days) and are shown in FIG. 14. These data demonstrated that ATT stabilized furimazine in DMSO against decomposition at different temperatures (e.g., room temperature, 40° C., and 60° C.).

Example 7

Stability of Furimazine at 37° C.

As described above, ATT stabilized furimazine against decomposition over time at different temperatures and in the presence of light. To further examine the stabilization of furimazine, luminescence was measured at 37° C. in the presence or absence of ATT and ATT analogs TAK-0014 and TAK-0002.

Specifically, a stock solution of furimazine in 50% propylene glycol:50% ethanol (v/v) was prepared, in which the final concentration of furimazine by absorbance was 4.6 mM. The furimazine stock solution was then diluted 1:1 in 50% propylene glycol:50% ethanol (v/v) to create a control solution without the additives ATT, TAK-0014 and TAK-0002 (i.e., "no additive furimazine" control) and containing 2.3 mM furimazine. 400 mM stock solutions of ATT, TAK-0014 and TAK-0002 were prepared in 50% propylene glycol:50% ethanol (v/v). Each of the ATT, TAK-0014 and TAK-0002 stock solutions was then diluted 1:1 in the 4.6 mM furimazine stock solution to yield solutions containing 200 mM ATT, TAK-0014 or TAK-0002, and 2.3 mM furimazine.

Each sample was separated into multiple amber tubes and incubated at 37° C. in a dark incubator (i.e., in the absence of light). Aliquots were taken from each sample at various time points and stored at −20° C. in the dark (i.e., in the absence of light) until all time points were collected.

Figure 15A:
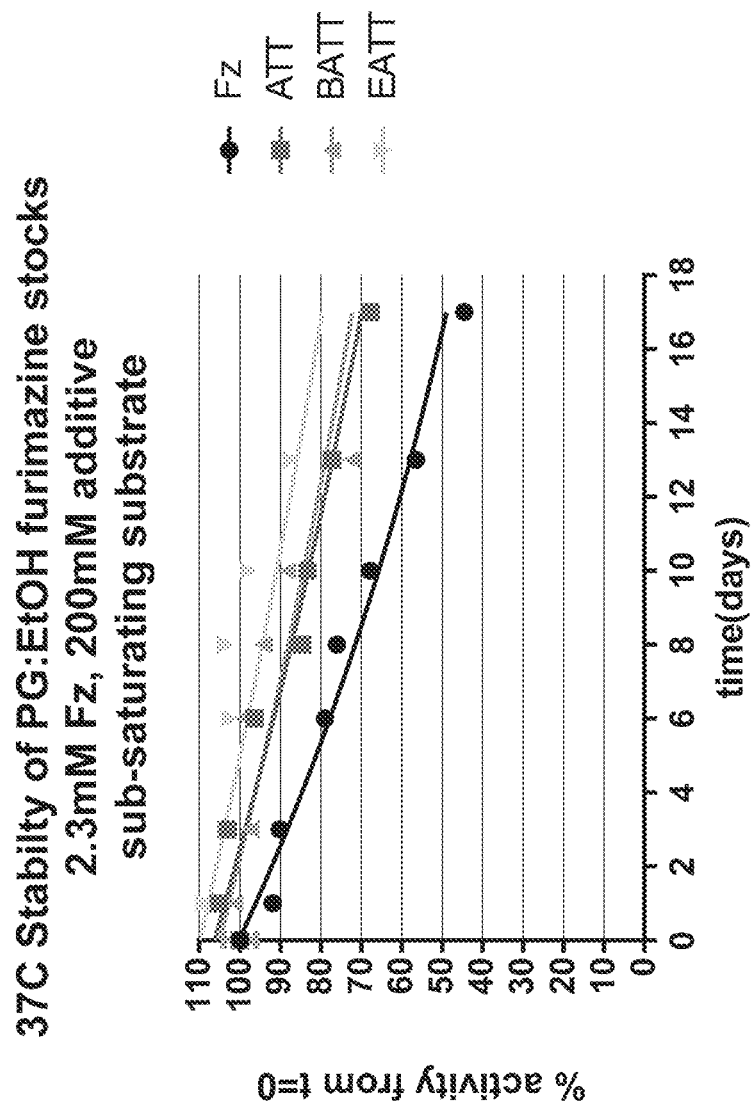
FIG. 15A shows the percent activity from time point 0 days (t=0) over time (days) for furimazine in the presence or absence of a thionucleoside.

To measure luminescence in the aliquots, each aliquot was diluted 1:50 in buffer (NANOGLO buffer, Promega Corporation) to yield 46 μM furimazine. These diluted aliquots were further diluted 1:10 in buffer (NANOGLO buffer, Promega Corporation) to yield 4.6 μM furimazine. 504 of each dilution (i.e., the twice diluted (0.1) aliquots) was mixed with 504, of $CO_2$-independent media+10% fetal bovine serum (FBS) and 0.4 ng/mL luminogenic enzyme (NANOLUC enzyme, Promega Corporation). Luminescence was measured on a luminometer (GLOMAX Multi Plus luminometer, Promega Corporation). Relative light units (RLUs) were normalized for each time point by the RLU value at the 0 days time point. The percent activity from the 0 days time point (i.e., t=0) was plotted against time (days) for each sample as shown in FIG. 15A. In FIG. 15A, B-ATT denoted TAK-0002 and E-ATT denoted TAK-0014.

Figure 15B:
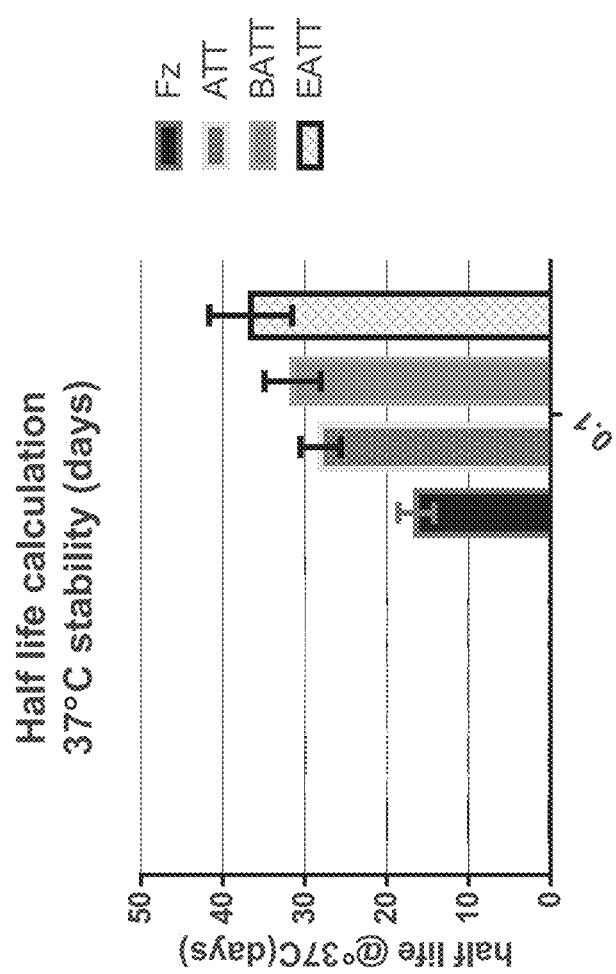
FIG. 15B shows the half-life at 37° C. in days for each sample in FIG. 15A.

The half-lives were calculated using GraphPad Prism software set to One Phase decay and are shown in Table 15 and FIG. 15B. Table 15 shows the half-lives calculated from the curves depicted in FIG. 15A (i.e., 0.1, which denoted the half-lives of the indicated twice diluted aliquots). Error in Table 15 was the standard error from a regression calculation and Fz denoted furimazine, B-ATT denoted TAK-0002, and E-ATT denoted TAK-0014.

FIG. 15B is a graph plotting half-life at 37° C. in days against sample, in which Fz denoted furimazine, B-ATT denoted TAK-0002, and E-ATT denoted TAK-0014. Also in FIG. 15B, 0.1 denoted the half-lives for the twice diluted aliquots.

TABLE 15

| | Fz | | | ATT | | | B-ATT | | | E-ATT | | |
|---|---|---|---|---|---|---|---|---|---|---|---|---|
| Sample | Mean | +Error | −Error | Mean | +Error | −Error | Mean | +Error | −Error | Mean | +Error | −Error |
| 0.1 | 16.42 | 2.180 | 2.180 | 28.12 | 2.453 | 2.453 | 31.52 | 3.432 | 3.432 | 36.62 | 5.047 | 5.047 |

As demonstrated in prior Examples, ATT stabilized furimazine against decomposition at different temperatures and in the presence of light. The results in this Example demonstrated an increased half-life of luminescence from furimazine when a thionucleoside such as ATT, TAK-0014, and TAK-0002 was added to an organic solvent (e.g., 50% propylene glycol:50% ethanol (v/v) containing furimazine. The results in this Example also demonstrated that a thionucleoside such as ATT, TAK-0014, and TAK-0002, stabilized furimazine against decomposition in the absence of light (i.e., in the dark). Together, these results indicated that the thionucleoside stabilized furimazine against decomposition, thereby allowing for an increased half-life of luminescence from furimazine.

Example 8

Stability of Furimazine at 37° C. in Different Organic Solvents

As described above, a thionucleoside such as ATT, TAK-0014, and TAK-0002, stabilized furimazine against decomposition over time at different temperatures, in the presence of light, and in the absence of light (i.e., in the dark). To further examine the stabilization of furimazine at 37° C., luminescence was measured after furimazine was incubated in the presence of different organic solvents, namely 50% (v/v) propylene glycol (PG):50% (v/v) ethanol, 60% (v/v) propylene glycol (PG):40% (v/v) ethanol, and 15% (v/v) glycerol:85% (v/v) ethanol.

Specifically, the materials employed in this study are shown in Table 16.

TABLE 16

| Component | Part Number | Lot Number | Supplier |
|---|---|---|---|
| ATT (6-Aza-2-thiothymine) | 82393 | BCBH7729V | Fluka |
| Propylene Glycol (PG) | P4347 | MKBN7334V | Sigma |
| 100% Ethanol | 111000200 | C1303262 | AAPER |
| Glycerol | G5516 | 08596LK | Sigma |
| Furimazine powder | 2-1210-26 | | Promega |
| 5 mM Furimazine stock ("Inventory Furimazine"; 15% glycerol: 85% ethanol, 5 mM furimazine, no ATT) | N113C | 88409 | Promega |

1.25 mM stocks of furimazine were prepared in the following solutions: a) 50% propylene glycol:50% ethanol, 1.25 mM furimazine, 250 mM ATT; b) 60% propylene glycol:40% ethanol, 1.25 mM furimazine, 300 mM ATT; c) 15% glycerol:85% ethanol, 1.25 mM furimazine, 250 mM ATT; and inventory furimazine (Promega Corporation). Furimazine was first dissolved and then ATT was added. To make 4 mL of each sample, 2 mg furimazine and 143 mg of ATT (250 mM ATT) was added. For 300 mM ATT, 171 mg of ATT was added.

A portion of these samples was aliquoted into amber Starstead tubes with O-rings and then placed at 37° C. Samples were removed and placed at −20° C. at different time-points and then assayed all at once. The remaining sample was placed at −20° C. in a 15 mL tube and monitored for precipitate formation.

Prior to assaying the samples, they were heated to room temperature (RT) and vortexed to ensure that any material that fell out of solution was re-suspended. 10 μl of each sample for each time-point was added to 490 μl buffer (NANOGLO buffer, Promega Corporation) and mixed to yield solutions with 25 μM furimazine. For inventory furimazine, 5 μl was diluted in 995 μl of buffer (NANOGLO buffer, Promega Corporation) to yield a solution with 25 μM furimazine. The 25 μM solutions were then diluted 1:100 (5 μl in 495 μl) to yield solutions with 0.25 μM furimazine (0.25 μM solutions). 50 μl of luciferase enzyme (NANOLUC luciferase, Promega Corporation) was diluted into $CO_2$-independent media+10% FBS with 50 μL of each of the 0.25 μM solutions. The resulting dilutions were incubated for 3 minutes at RT, and luminescence was detected on a luminometer (GLOMAX Multi plus luminometer, Promega Corporation). To assay for autoluminescence in the samples, samples were diluted 1:125 into $CO_2$-independent media+10% FBS (inventory furimazine was diluted 1:500), and luminescence detected on a luminometer (GLOMAX Multi plus luminometer, Promega Corporation).

Figure 16:
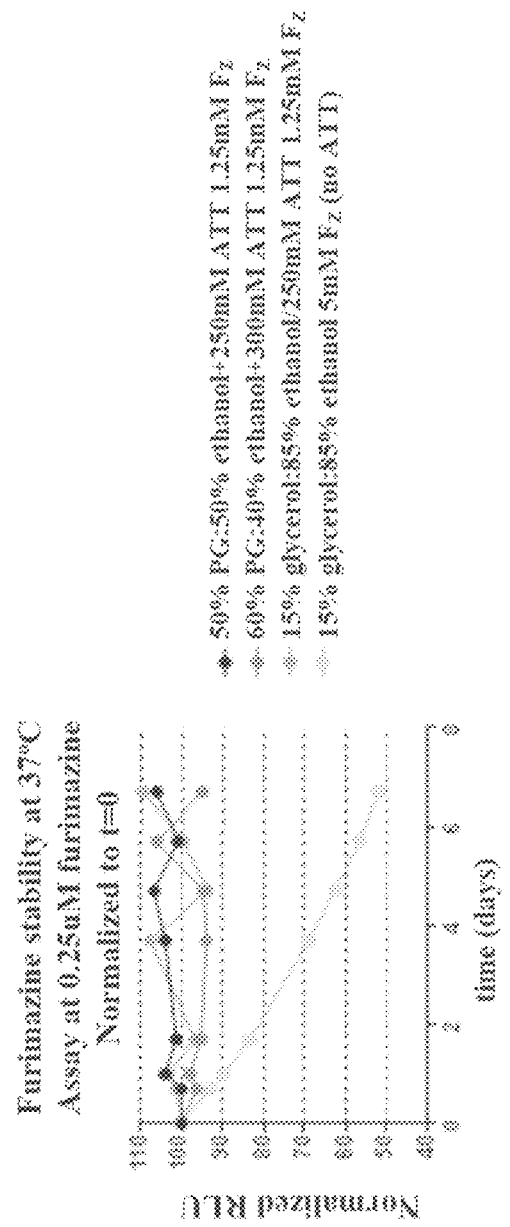
FIG. 16 shows normalized relative light units (RLUs), which were normalized to the timepoint 0 days (t=0), plotted against time (days) for 0.25 μM furimazine (Fz).

Relative light units (RLUs) were normalized for each time point by the RLU value at the 0 days time point (t=0). The normalized RLUs were plotted against time (days) for each sample as shown in FIG. 16 (0.25 μM solutions. These data demonstrated that furimazine was more stable in the presence of ATT than in the absence of ATT for each organic solvent. Furmazine was more stable in the organic solvent 15% glycerol:85% ethanol with ATT than in the organic solvent 15% glycerol:85% ethanol without ATT. Accordingly, these results, along with the results in the above Examples, demonstrated that ATT stabilized furimazine against decomposition at different temperatures, in the presence of light, in the absence of light, and in organic solvents such as DMSO, 50% (v/v) propylene glycol:50% (v/v) ethanol, and 15% glycerol (v/v):85% (v/v) ethanol. Together, these results indicated that the thionucleoside (e.g., ATT) stabilized furimazine against decomposition, thereby allowing for increased activity (i.e., luminescence) from furimazine.

6. Clauses

For reasons of completeness, various aspects of the invention are set out in the following numbered clauses:

Clause 1. A composition comprising (a) a luminogenic substrate; (b) an effective amount of a compound of formula (I) or a tautomer thereof,

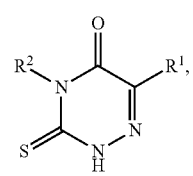

(I)

wherein

R¹ is hydrogen, alkyl, substituted alkyl, alkyl-aryl, alkyl-heteroaryl, cycloalkyl, aryl, heteroaryl, carboxylic acid, ester, NR$^a$R$^b$, imine, hydroxyl, or oxo;

R² is hydrogen, NR$^a$R$^b$, imine, alkyl, or aryl;

R$^a$ and R$^b$ are each independently hydrogen, alkyl, or aryl; and (c) an organic solvent.

Clause 2. The composition of clause 1, wherein the composition does not contain a luminogenic enzyme.

Clause 3. The composition of clause 1, wherein the luminogenic substrate is stabilized against decomposition.

Clause 4. The composition of clause 3, wherein the luminogenic substrate is stabilized against decomposition as compared to a composition that does not include the compound of formula (I) or tautomer thereof.

Clause 5. The composition of clause 3 or 4, wherein the luminogenic substrate is stabilized against decomposition in the presence of light.

Clause 6. The composition of clause 3 or 4, wherein the luminogenic substrate is stabilized against decomposition in the absence of light.

Clause 7. The composition of clause 3 or 4, wherein the luminogenic substrate is stabilized against decomposition at temperatures from −80° C. to 60° C.

Clause 8. The composition of clause 1, wherein the luminogenic substrate is coelenterazine or a functional analog thereof Clause 9. The composition of clause 8, wherein the coelenterazine or the functional analog thereof is stabilized against decomposition.

Clause 10. The composition of clause 9, wherein the coelenterazine or the functional analog thereof is stabilized against decomposition in the presence of light.

Clause 11. The composition of clause 10, wherein the coelenterazine or the functional analog thereof is stabilized against decomposition in the presence of light as compared to a composition that does not include the compound of formula (I) or tautomer thereof Clause 12. The composition of clause 9, wherein the coelenterazine or the functional analog thereof is stabilized against decomposition in the absence of light.

Clause 13. The composition of clause 12, wherein the coelenterazine or the functional analog thereof is stabilized against decomposition in the absence of light as compared to a composition that does not include the compound of formula (I) or tautomer thereof.

Clause 14. The composition of clause 9, wherein the coelenterazine or the functional analog thereof is stabilized against decomposition at temperatures from −80° C. to 60° C.

Clause 15. The composition of clause 8, wherein the functional analog of coelenterazine is furimazine.

Clause 16. The composition of clause 15, wherein furimazine is stabilized against decomposition in the presence of light.

Clause 17. The composition of clause 16, wherein furimazine is stabilized against decomposition in the presence of light as compared to a composition that does not include the compound of formula (I) or tautomer thereof.

Clause 18. The composition of clause 15, wherein furimazine is stabilized against decomposition in the absence of light.

Clause 19. The composition of clause 18, wherein furimazine is stabilized against decomposition in the absence of light as compared to a composition that does not include the compound of formula (I) or tautomer thereof.

Clause 20. The composition of clause 1, wherein the effective amount of the compound of formula (I) is greater than 0.1 mM.

Clause 21. The composition of clause 20, wherein the effective amount of the compound of formula (I) is greater than 1 mM.

Clause 22. The composition of clause 1, wherein the compound of formula (I) is selected from the group consisting of: ATT, ATCA, 3-(4-Amino-5-oxo-3-thioxo-2,3,4,5-tetrahydro-1,2,4-triazin-6-yl)propanoic acid, tetrahydro-2-methyl-3-thioxo-1,2,4-triazine-5,6-dione, 4-((2-furylmethylene)amino)-3-mercapto-6-methyl-1,2,4-triazin-5(4H)-one, 6-benzyl-3-sulfanyl-1,2,4-triazin-5-ol, 4-amino-3-mercapto-6-methyl-1,2,4-triazin-5(4H)-one, 3-(5-oxo-3-thioxo-2,3,4,5-tetrahydro-1,2,4-triazin-6-yl)propanoic acid, (E)-6-methyl-4-((thiophen-2-ylmethylene)amino)-3-thioxo-3,4-dihydro-1,2,4-triazin-5(2H)-one, (E)-6-methyl-4-((3-nitrobenzylidene)amino)-3-thioxo-3,4-dihydro-1,2,4-triazin-5 (2H)-one, (E)-4-44-(diethylamino)benzylidene)amino)-6-methyl-3-thioxo-3,4-dihydro-1,2,4-triazin-5(2H)-one, ATCA ethyl ester, TAK-0014, TAK-0002, TAK-0021, TAK-0020, TAK-0018, TAK-0009, TAK-0007, TAK-0008, TAK-0003, TAK-0004, 3-thioxo-6-(trifluoromethyl)-3,4-dihydro-1,2,4-triazin-5(2H)-one, 6-cyclopropyl-3-thioxo-3,4-dihydro-1,2,4-triazin-5(2H)-one, and 6-(hydroxymethyl)-3-thioxo-3,4-dihydro-1,2,4-triazin-5(2H)-one.

Clause 23. The composition of clause 22, wherein the compound of formula (I) is ATT and wherein the effective amount of ATT is greater than 32 mM.

Clause 24. The composition of clause 23, wherein the effective amount of ATT is 225 mM.

Clause 25. The composition of clause 1, wherein the organic solvent is selected from the group consisting of alcohol, propylene glycol, dimethyl sulfoxide (DMSO), acetonitrile, glycerol, and any combination thereof.

Clause 26. The composition of clause 25, wherein the organic solvent is a combination of ethanol and propylene glycol.

Clause 27. The composition of clause 25, wherein the organic solvent is a combination of ethanol and glycerol.

Clause 28. A method for stabilizing a luminogenic substrate, the method comprising contacting the luminogenic substrate with an effective amount of a compound of formula (I) or a tautomer thereof in the presence of an organic solvent, whereby the luminogenic substrate is stabilized against decomposition, wherein the compound of formula (I) is

(I)

wherein

R¹ is hydrogen, alkyl, substituted alkyl, alkyl-aryl, alkyl-heteroaryl, cycloalkyl, aryl, heteroaryl, carboxylic acid, ester, NR$^a$R$^b$, imine, hydroxyl, or oxo;

R² is hydrogen, NR$^a$R$^b$, imine, alkyl, or aryl; and

R$^a$ and R$^b$ are each independently hydrogen, alkyl, or aryl.

Clause 29. The method of clause 28, wherein the effective amount of the compound of formula (I) is greater than 0.1 mM.

Clause 30. The method of clause 29, wherein the effective amount of the compound of formula (I) is greater than 1 mM.

Clause 31. The method of clause 28, wherein the compound of formula (I) is selected from the group consisting of: ATT, ATCA, 3-(4-Amino-5-oxo-3-thioxo-2,3,4,5-tetrahydro-1,2,4-triazin-6-yl)propanoic acid, tetrahydro-2-methyl-3-thioxo-1,2,4-triazine-5,6-dione, 4((2-furylmethylene)amino)-3-mercapto-6-methyl-1,2,4-triazin-5(4H)-one, 6-benzyl-3-sulfanyl-1,2,4-triazin-5-ol, 4-amino-3-mercapto-6-methyl-1,2,4-triazin-5(4H)-one, 3-(5-oxo-3-thioxo-2,3,4,5-tetrahydro-1,2,4-triazin-6-yl)propanoic acid, (E)-6-methyl-4-((thiophen-2-ylmethylene)amino)-3-thioxo-3,4-dihydro-1,2,4-triazin-5(2H)-one, (E)-6-methyl-4-((3-nitrobenzylidene)amino)-3-thioxo-3,4-dihydro-1,2,4-triazin-5(2H)-one, (E)-4-((4-(diethylamino)benzylidene)amino)-6-methyl-3-thioxo-3,4-dihydro-1,2,4-triazin-5(2H)-one, ATCA ethyl ester, TAK-0014, TAK-0002, TAK-0021, TAK-0020, TAK-0018, TAK-0009, TAK-0007, TAK-0008, TAK-0003, TAK-0004, 3-thioxo-6-(trifluoromethyl)-3,4-dihydro-1,2,4-triazin-5(2H)-one, 6-cyclopropyl-3-thioxo-3,4-dihydro-1,2,4-triazin-5(2H)-one, and 6-(hydroxymethyl)-3-thioxo-3,4-dihydro-1,2,4-triazin-5(2H)-one.

Clause 32. The method of clause 31, wherein the compound of formula (I) is ATT and wherein the effective amount of the ATT is greater than 32 mM.

Clause 33. The method of clause 32, wherein the effective amount of the ATT is 225 mM.

Clause 34. The method of clause 28, wherein luminogenic substrate is stabilized against decomposition in the presence of light.

Clause 35. The method of clause 28, wherein the luminogenic substrate is stabilized against decomposition in the absence of light.

Clause 36. The method of clause 28, wherein the luminogenic substrate is stabilized against decomposition at temperatures from −80° C. to 60° C.

Clause 37. The method of clause 28, wherein the luminogenic substrate is coelenterazine or a functional analog thereof Clause 38. The method of clause 37, wherein the functional analog of coelenterazine is furimazine.

Clause 39. The method of clause 38, wherein furimazine is stabilized against decomposition in the presence of light.

Clause 40. The method of clause 38, wherein furimazine is stabilized against decomposition in the absence of light.

Clause 41. The method of clause 28, wherein the organic solvent is selected from the group consisting of alcohol, propylene glycol, dimethyl sulfoxide (DMSO), acetonitrile, glycerol, and any combination thereof.

Clause 42. The method of clause 41, wherein the organic solvent is a combination of ethanol and propylene glycol.

Clause 43. The method of clause 41, wherein the organic solvent is a combination of ethanol and glycerol.

Clause 44. A kit comprising the composition of clause 1 in a single container, wherein the compound of formula (I) stabilizes the luminogenic substrate.

Clause 45. The kit of clause 44, wherein the luminogenic substrate is coelenterazine or a functional analog thereof Clause 46. The kit of clause 45, wherein the functional analog of coelenterazine is furimazine.

Clause 47. The kit of clause 44, wherein the effective amount of the compound of formula (I) is greater than 0.1 mM.

Clause 48. The kit of clause 47, wherein the effective amount of the compound of formula (I) is greater than 1 mM.

Clause 49. The kit of clause 44, wherein the compound of formula (I) is selected from the group consisting of: ATT, ATCA, 3-(4-Amino-5-oxo-3-thioxo-2,3,4,5-tetrahydro-1,2,4-triazin-6-yl)propanoic acid, tetrahydro-2-methyl-3-thioxo-1,2,4-triazine-5,6-dione, 4((2-furylmethylene)amino)-3-mercapto-6-methyl-1,2,4-triazin-5(4H)-one, 6-benzyl-3-sulfanyl-1,2,4-triazin-5-ol, 4-amino-3-mercapto-6-methyl-1,2,4-triazin-5(4H)-one, 3-(5-oxo-3-thioxo-2,3,4,5-tetrahydro-1,2,4-triazin-6-yl)propanoic acid, (E)-6-methyl-4-((thiophen-2-ylmethylene)amino)-3-thioxo-3,4-dihydro-1,2,4-triazin-5(2H)-one, (E)-6-methyl-4-((3-nitrobenzylidene)amino)-3-thioxo-3,4-dihydro-1,2,4-triazin-5(2H)-one, (E)-4-((4-(diethylamino)benzylidene)amino)-6-methyl-3-thioxo-3,4-dihydro-1,2,4-triazin-5(2H)-one, ATCA ethyl ester, TAK-0014, TAK-0002, TAK-0021, TAK-0020, TAK-0018, TAK-0009, TAK-0007, TAK-0008, TAK-0003, TAK-0004, 3-thioxo-6-(trifluoromethyl)-3,4-dihydro-1,2,4-triazin-5(2H)-one, 6-cyclopropyl-3-thioxo-3,4-dihydro-1,2,4-triazin-5(2H)-one, and 6-(hydroxymethyl)-3-thioxo-3,4-dihydro-1,2,4-triazin-5(2H)-one.

Clause 50. The kit of clause 49, wherein the compound of formula (I) is ATT and the effective amount of ATT is greater than 32 mM.

Clause 51. The kit of clause 50, wherein the effective amount of ATT is 225 mM.

Clause 52. The kit of clause 44, wherein the organic solvent is selected from the group consisting of alcohol, propylene glycol, dimethyl sulfoxide (DMSO), acetonitrile, glycerol, and any combination thereof.

Clause 53. The kit of clause 52, wherein the organic solvent is a combination of ethanol and propylene glycol.

Clause 54. The kit of clause 53, wherein the organic solvent is a combination of ethanol and propylene glycol.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:
1. A composition comprising
(a) a luminogenic substrate;
(b) an effective amount of a compound of formula (I) or a tautomer thereof,

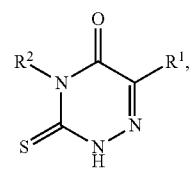

wherein
R$^1$ is hydrogen, alkyl, substituted alkyl, alkyl-aryl, alkyl-heteroaryl, cycloalkyl, aryl, heteroaryl, carboxylic acid, ester, NR$^a$R$^b$, imine, hydroxyl, or oxo;
R$^2$ is hydrogen, NR$^a$R$^b$, imine, alkyl, or aryl;

Rᵃ and Rᵇ are each independently hydrogen, alkyl, or aryl; and (c) an organic solvent;
wherein the luminogenic substrate is coelenterazine or a functional analog thereof.

2. The composition of claim 1, wherein the composition does not contain a luminogenic enzyme.

3. The composition of claim 1, wherein the luminogenic substrate is stabilized against decomposition in the presence of light, in the absence of light, or at temperatures from −80° C. to 60° C.

4. The composition of claim 1, wherein the functional analog of coelenterazine is furimazine.

5. The composition of claim 1, wherein the effective amount of the compound of formula (I) is greater than 0.1 mM.

6. The composition of claim 1, wherein the compound of formula (I) is selected from the group consisting of: ATT, ATCA, 3-(4-Amino-5-oxo-3-thioxo-2,3,4,5-tetrahydro-1,2,4-triazin-6-yl)propanoic acid, tetrahydro-2-methyl-3-thioxo-1,2,4-triazine-5,6-dione, 4-((2-furylmethylene)amino)-3-mercapto-6-methyl-1,2,4-triazin-5(41-1)-one, 6-benzyl-3-sulfanyl-1,2,4-triazin-5-ol, 4-amino-3-mercapto-6-methyl-1,2,4-triazin-5(4H)-one, 3-(5-oxo-3-thioxo-2,3,4,5-tetrahydro-1,2,4-triazin-6-yl)propanoic acid, (E)-6-methyl-4-((thiophen-2-ylmethylene)amino)-3-thioxo-3,4-dihydro-1,2,4-triazin-5(2H)-one, (E)-6-methyl-4-((3-nitrobenzylidene)amino)-3-thioxo -3,4-dihydro-1,2,4-triazin-5(2H)-one, (E)-4-((4-(diethylamino)benzylidene)amino)-6-methyl-3-thioxo -3,4-dihydro-1,2,4-triazin-5(2H)-one, ATCA ethyl ester, TAK-0014, TAK-0002, TAK-0021, TAK -0020, TAK-0018, TAK-0009, TAK-0007, TAK-0008, TAK-0003, TAK-0004, 3-thioxo-6-(trifluoromethyl)-3,4-dihydro-1,2,4-triazin-5(2H)-one, 6-cyclopropyl-3-thioxo-3,4-dihydro-1,2,4-triazin-5(2H)-one, and 6-(hydroxymethyl)-3-thioxo-3,4-dihydro-1,2,4-triazin-5(2H) -one.

7. The composition of claim 6, wherein the compound of formula (I) is ATT and wherein the effective amount of ATT is greater than 32 mM.

8. The composition of claim 1, wherein the organic solvent is selected from the group consisting of alcohol, propylene glycol, dimethyl sulfoxide (DMSO), acetonitrile, glycerol, and any combination thereof.

9. The composition of claim 8, wherein the organic solvent is a combination of ethanol and propylene glycol or a combination of ethanol and glycerol.

10. A method for stabilizing a luminogenic substrate, the method comprising contacting the luminogenic substrate with an effective amount of a compound of formula (I) or a tautomer thereof in the presence of an organic solvent, whereby the luminogenic substrate is stabilized against decomposition,
wherein the luminogenic substrate is coelenterazine or a functional analog thereof;
wherein the compound of formula (I) is

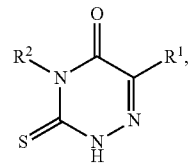

wherein
R¹ is hydrogen, alkyl, substituted alkyl, alkyl-aryl, alkyl-heteroaryl, cycloalkyl, aryl, heteroaryl, carboxylic acid, ester, NRᵃRᵇ, imine, hydroxyl, or oxo;
R² is hydrogen, NRᵃRᵇ, imine, alkyl, or aryl; and
Rᵃ and Rᵇ are each independently hydrogen, alkyl, or aryl.

11. The method of claim 10, wherein the effective amount of the compound of formula (I) is greater than 0.1 mM.

12. The method of claim 10, wherein the compound of formula (I) is selected from the group consisting of: ATT, ATCA, 3-(4-Amino-5-oxo-3-thioxo-2,3,4,5-tetrahydro-1,2,4-triazin-6-yl)propanoic acid, tetrahydro-2-methyl-3-thioxo-1,2,4-triazine-5,6-dione, 4-((2-furylmethylene)amino)-3-mercapto-6-methyl-1,2,4-triazin-5(4H)-one, 6-benzyl-3-sulfanyl-1,2,4-triazin-5-ol, 4-amino-3-mercapto-6-methyl-1,2,4-triazin-5(4H)-one, 3-(5-oxo-3-thioxo-2,3,4,5-tetrahydro-1,2,4-triazin-6-yl)propanoic acid, (E)-6-methyl-4-((thiophen-2-ylmethylene)amino)-3-thioxo-3,4-dihydro-1,2,4-triazin-5(2H)-one, (E)-6-methyl-4-((3-nitrobenzylidene)amino)-3-thioxo -3,4-dihydro-1,2,4-triazin-5(2H)-one, (E)-4-((4-(diethylamino)benzylidene)amino)-6-methyl-3-thioxo -3,4-dihydro-1,2,4-triazin-5(2H)-one, ATCA ethyl ester, TAK-0014, TAK-0002, TAK-0021, TAK -0020, TAK-0018, TAK-0009, TAK-0007, TAK-0008, TAK-0003, TAK-0004, 3-thioxo-6-(trifluoromethyl)-3,4-dihydro-1,2,4-triazin-5(2H) -one, 6-cyclopropyl-3-thioxo-3,4-dihydro-1,2,4-triazin-5(2H) -one, and 6-(hydroxymethyl)-3-thioxo-3,4-dihydro-1,2,4-triazin-5(2H) -one.

13. The method of claim 12, wherein the compound of formula (I) is ATT and wherein the effective amount of the ATT is greater than 32 mM.

14. The method of claim 10, wherein luminogenic substrate is stabilized against decomposition in the presence of light, in the absence of light, or at temperatures from −80° C. to 60° C.

15. The method of claim 10, wherein the functional analog of coelenterazine is furimazine.

16. The method of claim 10, wherein the organic solvent is selected from the group consisting of alcohol, propylene glycol, dimethyl sulfoxide (DMSO), acetonitrile, glycerol, and any combination thereof.

17. A kit comprising the composition of claim 1 in a single container, wherein the compound of formula (I) stabilizes the luminogenic substrate.

* * * * *